(12) United States Patent
Zhang et al.

(10) Patent No.: US 11,331,184 B2
(45) Date of Patent: *May 17, 2022

(54) METHODS AND DEVICES FOR DELIVERY OF A PROSTHETIC VALVE

(71) Applicant: JC Medical, Inc., Burlingame, CA (US)

(72) Inventors: Ji Zhang, Burnaby (CA); Brandon G. Walsh, Kaysville, UT (US); Cheng Yong Yang, Foster City, CA (US)

(73) Assignee: JC Medical, Inc., Burlingame, CA (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/240,458

(22) Filed: Jan. 4, 2019

(65) Prior Publication Data

US 2019/0209318 A1 Jul. 11, 2019

Related U.S. Application Data

(60) Provisional application No. 62/614,488, filed on Jan. 7, 2018.

(51) Int. Cl.
*A61F 2/24* (2006.01)
*A61F 2/966* (2013.01)
*A61M 25/01* (2006.01)

(52) U.S. Cl.
CPC .......... *A61F 2/2436* (2013.01); *A61F 2/2463* (2013.01); *A61F 2/246* (2013.01);
(Continued)

(58) Field of Classification Search
CPC ...... A61F 2/2436; A61F 2/243; A61F 2/2427; A61F 2/962; A61F 2/966; A61F 2/2439;
(Continued)

(56) References Cited

U.S. PATENT DOCUMENTS 5,261,263 A 11/1993 Whitesell
6,202,272 B1 3/2001 Jackson
(Continued)

FOREIGN PATENT DOCUMENTS

CN 1631338 6/2005
CN 102083392 6/2011
(Continued)

OTHER PUBLICATIONS

International Search Report and Written Opinion from PCT/US2019/012408, dated Apr. 8, 2019, 11 pages.

*Primary Examiner* — Katherine H Schwiker
(74) *Attorney, Agent, or Firm* — Nathan S. Smith; Sujohn Das; Morgan, Lewis & Bockius LLP

(57) ABSTRACT

Methods of assembling and delivering a valve prosthesis and delivery system are disclosed herein. A method can include housing a valve prosthesis in a compacted state within a sheath of a delivery system. The valve prosthesis can include a valve anchor and a support frame coupled to the valve anchor, and the valve anchor can include a plurality of anchoring legs having a plurality of connection apertures. The method can further include slidably coupling a pin assembly around a core member so that the pin assembly is slidable longitudinally along the core member, and inserting a plurality of pins of the pin assembly through the plurality of connection apertures of the valve anchor and a plurality of lock apertures of the delivery system to engage the plurality of anchoring legs of the valve anchor.

7 Claims, 14 Drawing Sheets

(52) U.S. Cl.
CPC ............. *A61F 2/2433* (2013.01); *A61F 2/966* (2013.01); *A61F 2002/9665* (2013.01); *A61F 2250/0063* (2013.01); *A61M 25/0136* (2013.01)

(58) Field of Classification Search
CPC ...... A61F 2002/9665; A61F 2002/9505; A61F 2002/9511
See application file for complete search history.

(56) References Cited

U.S. PATENT DOCUMENTS

| | | |
|---|---|---|
| 6,309,383 B1 | 10/2001 | Campbell et al. |
| 6,568,235 B1 | 5/2003 | Kokish |
| 7,011,671 B2 | 3/2006 | Welch |
| 7,018,406 B2 | 3/2006 | Seguin et al. |
| 7,044,966 B2 | 5/2006 | Svanidze et al. |
| 7,070,616 B2 | 7/2006 | Majercak et al. |
| 7,347,869 B2 | 3/2008 | Hojeibane et al. |
| 7,748,389 B2 | 7/2010 | Salahieh et al. |
| 7,914,575 B2 | 3/2011 | Guyenot et al. |
| 7,947,075 B2 | 5/2011 | Goetz et al. |
| 7,959,666 B2 | 6/2011 | Salahieh et al. |
| 8,052,750 B2 | 11/2011 | Tuval et al. |
| 8,303,653 B2 | 11/2012 | Bonhoeffer et al. |
| 8,348,995 B2 | 1/2013 | Tuval et al. |
| 8,348,996 B2 | 1/2013 | Tuval et al. |
| 8,353,953 B2 | 1/2013 | Giannetti et al. |
| 8,403,981 B2 | 3/2013 | Forster et al. |
| 8,414,643 B2 | 4/2013 | Tuval et al. |
| 8,540,767 B2 | 9/2013 | Zhang |
| 8,585,755 B2 | 11/2013 | Chau et al. |
| 8,585,756 B2 | 11/2013 | Bonhoeffer et al. |
| 8,652,204 B2 | 2/2014 | Quill et al. |
| 8,657,872 B2 | 2/2014 | Seguin |
| 8,685,085 B2 | 4/2014 | Guyenot et al. |
| 8,728,155 B2 | 5/2014 | Montorfano et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,795,356 B2 | 8/2014 | Quadri et al. |
| 8,834,564 B2 | 9/2014 | Tuval et al. |
| 8,840,661 B2 | 9/2014 | Manasse |
| 8,870,950 B2 | 10/2014 | Hacohen |
| 8,876,894 B2 | 11/2014 | Tuval et al. |
| 8,876,895 B2 | 11/2014 | Tuval et al. |
| 8,961,597 B2 | 2/2015 | Subramanian et al. |
| 8,992,604 B2 | 3/2015 | Gross et al. |
| 9,017,399 B2 | 4/2015 | Gross et al. |
| 9,050,188 B2 | 6/2015 | Schweich, Jr. et al. |
| 9,078,747 B2 | 7/2015 | Conklin |
| 9,132,009 B2 | 9/2015 | Hacohen et al. |
| 9,138,312 B2 | 9/2015 | Tuval et al. |
| 9,186,249 B2 | 11/2015 | Rolando et al. |
| 9,248,014 B2 | 2/2016 | Lane et al. |
| 9,301,834 B2 | 4/2016 | Tuval et al. |
| 9,308,087 B2 | 4/2016 | Lane et al. |
| 9,339,378 B2 | 5/2016 | Quadri et al. |
| 9,339,386 B2 | 5/2016 | Guyenot et al. |
| 9,387,071 B2 | 7/2016 | Tuval et al. |
| 9,387,078 B2 | 7/2016 | Gross et al. |
| 9,393,114 B2 | 7/2016 | Sutton et al. |
| 9,421,094 B2 | 8/2016 | Schweich, Jr. et al. |
| 9,427,315 B2 | 8/2016 | Schweich, Jr. et al. |
| 9,433,500 B2 | 9/2016 | Chau et al. |
| 9,445,897 B2 | 9/2016 | Bishop et al. |
| 9,474,599 B2 | 10/2016 | Keranen |
| 9,486,313 B2 | 11/2016 | Stacchino et al. |
| 9,492,273 B2 | 11/2016 | Wallace et al. |
| 9,554,903 B2 | 1/2017 | Rowe et al. |
| 9,561,103 B2 | 2/2017 | Granada et al. |
| 9,572,665 B2 | 2/2017 | Lane et al. |
| 9,579,199 B2 | 2/2017 | Hauser et al. |
| 9,585,751 B2 | 3/2017 | Morriss et al. |
| 9,622,858 B2 | 4/2017 | Annest |
| 9,622,863 B2 | 4/2017 | Karapetian et al. |
| 9,629,716 B2 | 4/2017 | Seguin |
| 9,642,704 B2 | 5/2017 | Tuval et al. |
| 9,649,212 B2 | 5/2017 | Fargahi |
| 9,675,454 B2 | 6/2017 | Vidlund et al. |
| 9,750,605 B2 | 9/2017 | Ganesan et al. |
| 9,750,606 B2 | 9/2017 | Ganesan et al. |
| 9,763,657 B2 | 9/2017 | Hacohen et al. |
| 9,763,778 B2 | 9/2017 | Eidenschink et al. |
| 9,763,782 B2 | 9/2017 | Solem |
| 9,770,329 B2 | 9/2017 | Lane et al. |
| 9,782,256 B2 | 10/2017 | Zeng et al. |
| 9,788,931 B2 | 10/2017 | Giordano et al. |
| 9,788,941 B2 | 10/2017 | Hacohen |
| 9,801,715 B2 | 10/2017 | Kovalsky |
| 9,827,097 B2 | 11/2017 | Tuval et al. |
| 9,833,315 B2 | 12/2017 | Vidlund et al. |
| 9,861,473 B2 | 1/2018 | Lafontaine |
| 9,861,475 B2 | 1/2018 | Machold et al. |
| 9,861,479 B2 | 1/2018 | Conklin |
| 9,867,695 B2 | 1/2018 | Stacchino et al. |
| 9,907,652 B2 | 3/2018 | Chau et al. |
| 9,913,714 B2 | 3/2018 | Tuval et al. |
| 9,913,716 B2 | 3/2018 | Cartledge et al. |
| 9,918,835 B2 | 3/2018 | Guyenot et al. |
| 9,931,204 B2 | 4/2018 | Rothstein et al. |
| 9,956,075 B2 | 5/2018 | Salahieh et al. |
| 9,962,259 B2 | 5/2018 | Leo et al. |
| 9,974,647 B2 | 5/2018 | Ganesan et al. |
| 9,974,651 B2 | 5/2018 | Hariton et al. |
| 10,004,599 B2 | 6/2018 | Rabito et al. |
| 10,004,601 B2 | 6/2018 | Tuval et al. |
| 10,010,414 B2 | 7/2018 | Cooper et al. |
| 10,010,417 B2 | 7/2018 | Keidar |
| 10,034,747 B2 | 7/2018 | Harewood |
| 10,034,749 B2 | 7/2018 | Spence et al. |
| 10,052,199 B2 | 8/2018 | Spence et al. |
| 10,052,204 B2 | 8/2018 | McLean et al. |
| 10,064,718 B2 | 9/2018 | Keidar |
| 10,085,837 B2 | 10/2018 | Keidar et al. |
| 10,098,733 B2 | 10/2018 | Righini |
| 10,117,741 B2 | 11/2018 | Schweich, Jr. et al. |
| 10,130,468 B2 | 11/2018 | Rowe et al. |
| 10,143,550 B2 | 12/2018 | Achiluzzi |
| 10,143,552 B2 | 12/2018 | Wallace et al. |
| 10,149,759 B2 | 12/2018 | Naor |
| 10,179,042 B2 | 1/2019 | Braido et al. |
| 10,188,517 B2 | 1/2019 | Gainor et al. |
| 10,195,033 B2 | 2/2019 | Tuval et al. |
| 10,265,166 B2 | 4/2019 | Schweich, Jr. et al. |
| 10,265,172 B2 | 4/2019 | Krivoruchko |
| 10,278,820 B2 | 5/2019 | Bar et al. |
| 10,321,992 B2 | 6/2019 | Quill et al. |
| 10,327,899 B2 | 6/2019 | Sandstrom et al. |
| 10,350,062 B2 | 7/2019 | Peterson et al. |
| 10,363,133 B2 | 7/2019 | Lane et al. |
| 10,383,724 B2 | 8/2019 | Seguin |
| 10,413,408 B2 | 9/2019 | Krone et al. |
| 10,433,952 B2 | 10/2019 | Lane et al. |
| 10,433,961 B2 | 10/2019 | McLean et al. |
| 10,449,039 B2 | 10/2019 | Ganesan et al. |
| 10,449,041 B2 | 10/2019 | Modine et al. |
| 10,449,043 B2 | 10/2019 | O'Connor et al. |
| 10,463,489 B2 | 11/2019 | Christianson et al. |
| 10,470,876 B2 | 11/2019 | Gurovich et al. |
| 10,500,038 B1 | 12/2019 | Orlov |
| 10,512,456 B2 | 12/2019 | Hacohen et al. |
| 10,531,872 B2 | 1/2020 | Hacohen et al. |
| 10,543,077 B2 | 1/2020 | Tuval et al. |
| 10,543,081 B2 | 1/2020 | Naor et al. |
| 10,543,084 B2 | 1/2020 | Guyenot et al. |
| 10,555,808 B2 | 2/2020 | Wallace et al. |
| 10,555,812 B2 | 2/2020 | Duffy et al. |
| 10,575,951 B2 | 3/2020 | Johnson et al. |
| 10,583,002 B2 | 3/2020 | Lane et al. |
| 10,583,005 B2 | 3/2020 | Calomeni et al. |
| 10,617,520 B2 | 4/2020 | Rowe et al. |
| 10,624,740 B2 | 4/2020 | Perszyk |
| 10,631,977 B2 | 4/2020 | Tayeb et al. |

(56) References Cited

U.S. PATENT DOCUMENTS

| | | | |
|---|---|---|---|
| 10,639,143 B2 | 5/2020 | Oba et al. | |
| 10,646,333 B2 | 5/2020 | Rothstein et al. | |
| 10,646,340 B2 | 5/2020 | Manash et al. | |
| 10,667,905 B2 | 6/2020 | Ekvall et al. | |
| 10,716,668 B2 | 7/2020 | Quill | |
| 10,729,541 B2 | 8/2020 | Francis et al. | |
| 10,736,736 B2 | 8/2020 | Schweich, Jr. et al. | |
| 10,743,988 B2 | 8/2020 | Seguin et al. | |
| 10,786,352 B2 | 9/2020 | Francis et al. | |
| 10,799,343 B2 | 10/2020 | Rothstein et al. | |
| 10,813,750 B2 | 10/2020 | Costello | |
| 10,813,752 B2 | 10/2020 | Seguin | |
| 10,813,757 B2 | 10/2020 | Cooper et al. | |
| 10,828,150 B2 | 11/2020 | Tamir | |
| 10,849,746 B2 | 12/2020 | Gregg et al. | |
| 10,869,758 B2 | 12/2020 | Ganesan et al. | |
| 10,898,325 B2 | 1/2021 | Calomeni et al. | |
| 10,959,840 B2 | 3/2021 | Whitman | |
| 10,966,824 B2 | 4/2021 | Zhang et al. | |
| 10,966,829 B2 | 4/2021 | Poppe et al. | |
| 10,973,634 B2 | 4/2021 | Cohen et al. | |
| 11,007,057 B2 | 5/2021 | Pham et al. | |
| 11,058,535 B2 | 7/2021 | Noe et al. | |
| 2003/0176912 A1 | 9/2003 | Chuter | |
| 2004/0093063 A1* | 5/2004 | Wright | A61F 2/95 623/1.12 |
| 2004/0128818 A1 | 7/2004 | Motsenbocker | |
| 2005/0075726 A1 | 4/2005 | Svanidze | |
| 2007/0068216 A1 | 3/2007 | Kokish | |
| 2008/0071361 A1 | 3/2008 | Tuval et al. | |
| 2008/0262590 A1 | 10/2008 | Murray | |
| 2008/0264102 A1* | 10/2008 | Berra | A61F 2/07 63/1.11 |
| 2009/0099637 A1 | 4/2009 | Barthold | |
| 2009/0216310 A1 | 8/2009 | Straubinger et al. | |
| 2009/0240320 A1 | 9/2009 | Tuval et al. | |
| 2009/0270971 A1 | 10/2009 | Xiao | |
| 2010/0234932 A1* | 9/2010 | Arbefeuille | A61F 2/95 623/1.11 |
| 2010/0249915 A1 | 9/2010 | Zhang | |
| 2010/0268315 A1* | 10/2010 | Glynn | A61F 2/95 623/1.11 |
| 2011/0022157 A1 | 1/2011 | Essinger | |
| 2011/0257720 A1* | 10/2011 | Peterson | A61F 2/95 623/1.11 |
| 2011/0264203 A1 | 10/2011 | Dwork | |
| 2012/0071969 A1 | 3/2012 | Li | |
| 2013/0213185 A1 | 8/2013 | Brown | |
| 2013/0274860 A1* | 10/2013 | Argentine | A61F 2/9517 623/1.12 |
| 2016/0067040 A1 | 3/2016 | Agrawal et al. | |
| 2017/0209268 A1 | 7/2017 | Cunningham et al. | |
| 2017/0218382 A1 | 10/2017 | Losetter | |
| 2018/0025311 A1 | 1/2018 | Thomas | |
| 2018/0338832 A1 | 11/2018 | Ganesan et al. | |
| 2019/0000615 A1 | 1/2019 | Tayeb et al. | |
| 2019/0015202 A1 | 1/2019 | Hacohen | |
| 2019/0029854 A1 | 1/2019 | Calomeni et al. | |
| 2019/0183643 A1* | 6/2019 | Yao | A61F 2/2436 |

FOREIGN PATENT DOCUMENTS

| | | |
|---|---|---|
| EP | 2319458 B1 | 4/2013 |
| EP | 2068767 B1 | 7/2015 |
| EP | 2544626 B1 | 10/2015 |
| EP | 2237746 B1 | 5/2016 |
| EP | 2618779 B1 | 8/2016 |
| EP | 3060173 A | 8/2016 |
| EP | 3085340 | 10/2016 |
| EP | 2032080 B1 | 5/2017 |
| EP | 3025682 B1 | 5/2017 |
| EP | 3294221 A | 3/2018 |
| EP | 3372199 A1 | 9/2018 |
| EP | 3415119 A1 | 12/2018 |
| FR | 2779939 | 12/1999 |
| JP | 2010-503497 | 2/2010 |
| JP | 2015-128626 | 7/2015 |
| WO | WO 2005/002466 | 1/2005 |
| WO | WO 2010/121076 | 10/2010 |
| WO | WO 2012/095445 | 7/2012 |
| WO | WO 2013/059747 | 4/2013 |
| WO | WO 2018/055389 | 3/2018 |
| WO | WO 2018/099484 | 6/2018 |
| WO | WO 2018/187805 | 10/2018 |
| WO | WO 2018/217525 | 11/2018 |

* cited by examiner

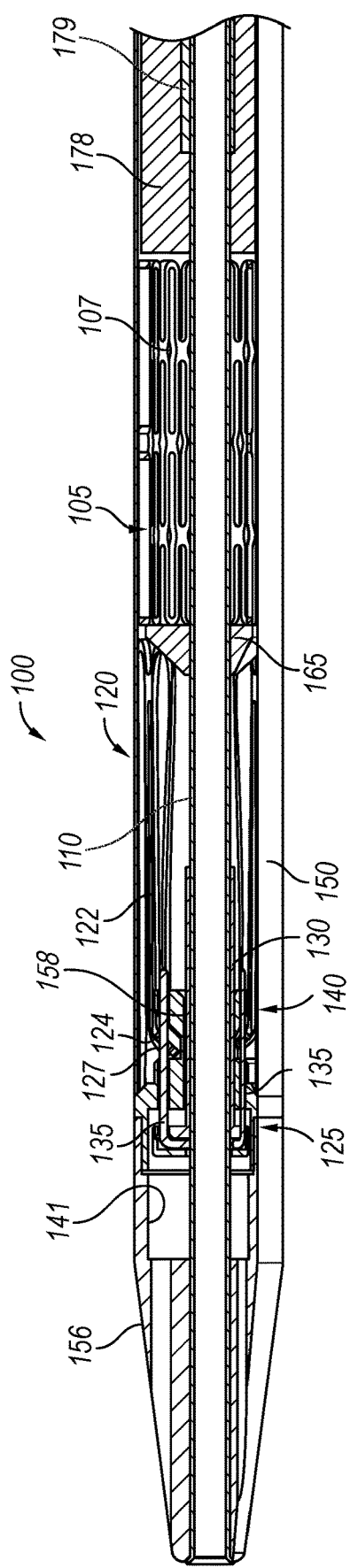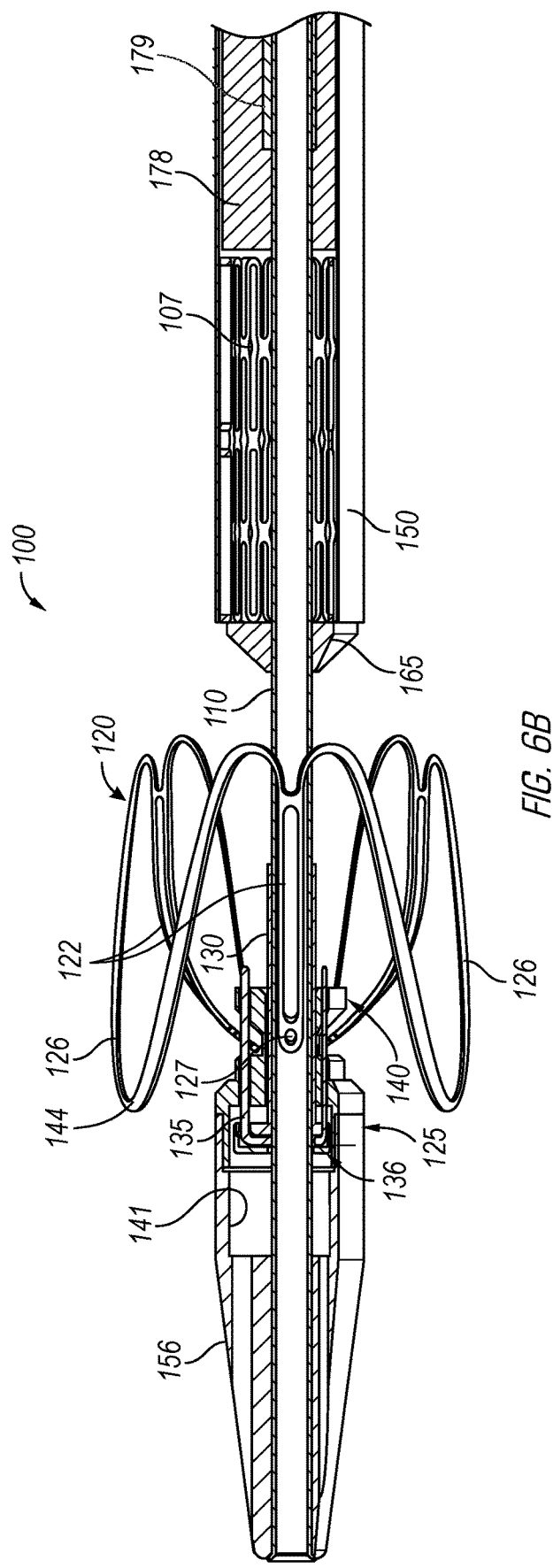

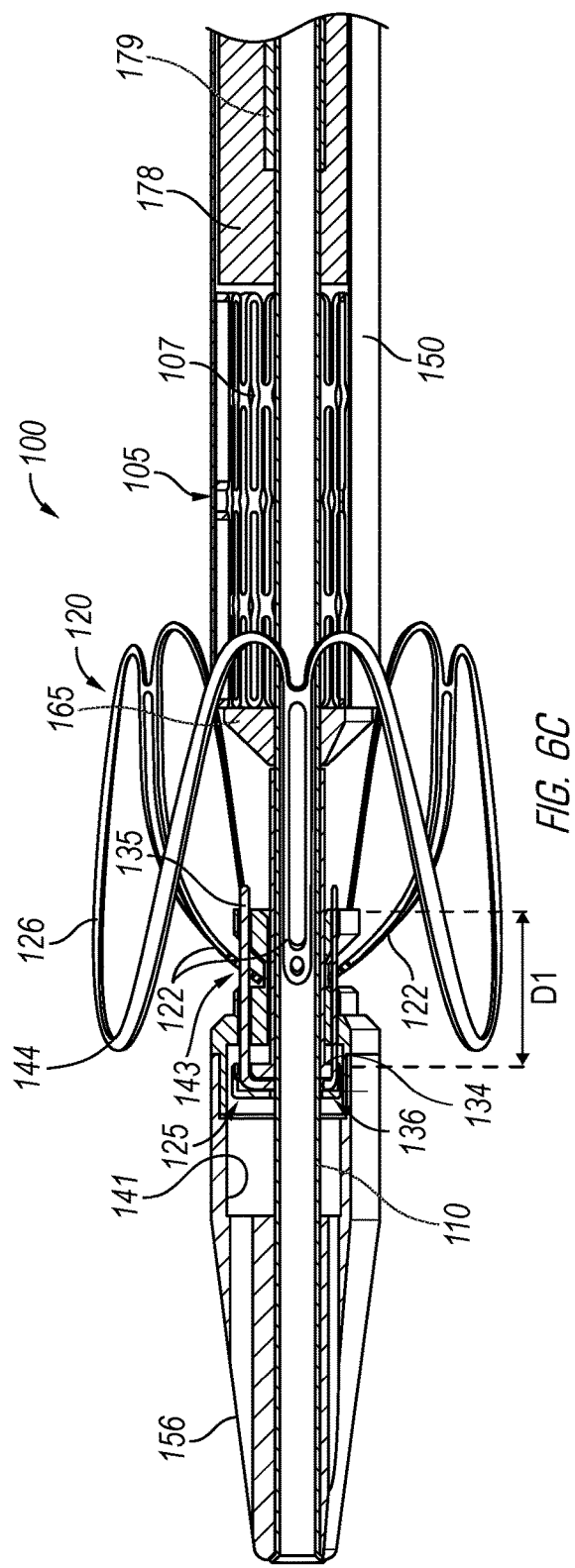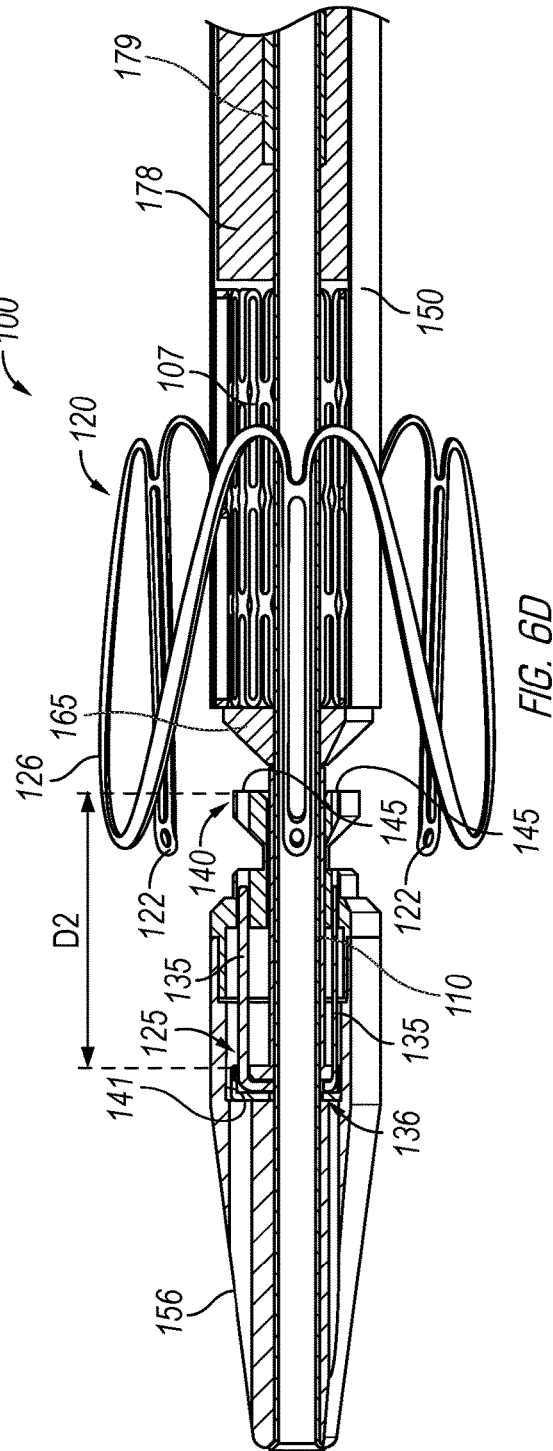

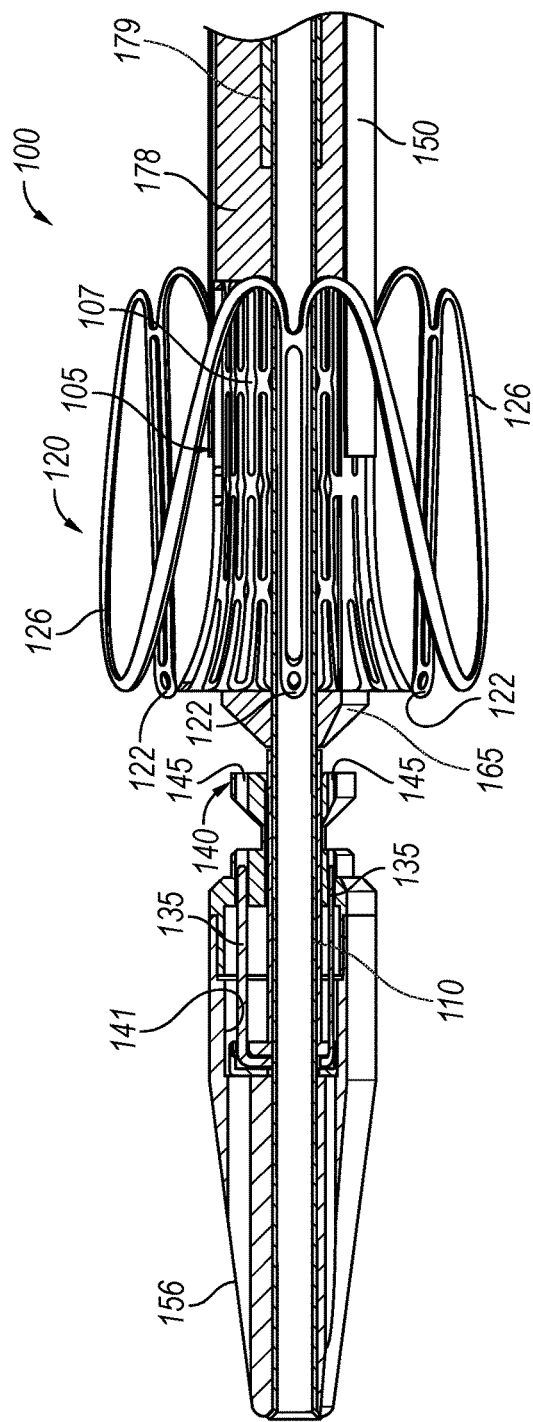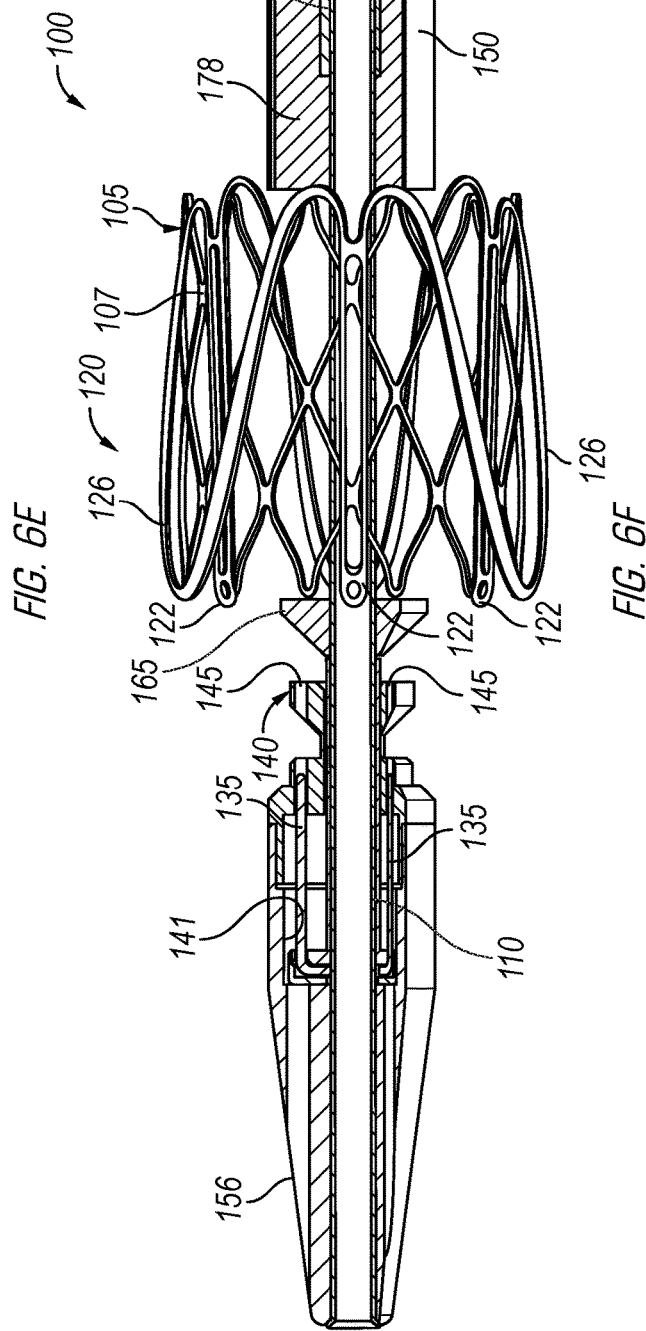

METHODS AND DEVICES FOR DELIVERY OF A PROSTHETIC VALVE

CROSS-REFERENCE TO RELATED APPLICATIONS

The present application claims the benefit of and priority to U.S. Provisional Application No. 62/614,488, filed on Jan. 7, 2018, the entirety of which is incorporated herein by reference.

BACKGROUND

Field of the Inventions

The present subject matter described herein relates to prosthetic heart valve delivery systems and methods for transcatheter delivery of a valve through the venous system.

Description of the Related Art

Prosthetic heart valves are used to replace damaged or diseased heart valves. In vertebrate animals, the heart is a muscular organ with four pumping chambers: the left and right atria and the left and right ventricles each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is more common since they reside in the left side of the heart where pressures are the greatest.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass, which involves stopping the heart to permit access to the internal chambers. Such open-heart surgery is particularly invasive and involves a lengthy and difficult recovery period.

Percutaneous delivery of an aortic valve has recently emerged as a promising alternative to surgical valve replacement. Presently, transcatheter implantation is accomplished by a transfemoral pathway with retrograde access to the native aortic valve. This minimally invasive aortic valve replacement has resulted in decreased hospitalization, reduction in sternal wound complications, reduced surgical trauma and improved cosmesis. Despite the success of transcatheter delivery through the femoral artery, there are significant drawbacks, especially in the elderly population, which is a population that benefits greatly from minimally invasive procedures.

In some patients, arterial diameter is too small to safely accommodate passage of a delivery system due to the buildup of plaque and the presence of stents previously implanted. Dislodging of plaque material during a transcatheter procedure can result in generation of emboli leading to risk of stroke. Accordingly, it is desirable to devise additional systems to allow transcatheter delivery of a valve prosthesis through the venous system, which generally has a larger inner diameter and can better accommodate the compact delivery system.

The foregoing examples of the related art and limitations related therewith are intended to be illustrative and not exclusive. Other limitations of the related art will become apparent to those of skill in the art upon a reading of the specification and a study of the drawings.

SUMMARY

The following aspects and some embodiments thereof described and illustrated below are meant to be exemplary and illustrative, not limiting in scope.

Transcatheter delivery of a valve prosthesis to the heart traditionally involves delivery through the vena cava and through the chambers of the heart. Due to the heart structure, such delivery requires that the system catheters be able to maneuver tight turns without damaging the surrounding tissue or the system itself. Described below are prosthetic valve delivery systems, valve prostheses, and methods of using the same, which provide increased flexibility for such transcatheter delivery in addition to the reduced diameter, which makes transcatheter delivery possible. Further, such systems, valve prostheses, and methods permit a clinician to more easily control expansion, placement, and release of a valve prosthesis. Further, some embodiments provide for systems and valve prostheses that can be delivered in a radially compact delivery configuration that achieves numerous advantages over conventional systems and devices, as described herein.

Some embodiments disclosed herein provide a delivery system for delivering a valve prosthesis. The valve prosthesis can comprise a radially expandable valve anchor, a support frame positionable within the valve anchor, and a plurality of valve leaflets coupled to the support frame. The delivery system can comprise a core member and an engagement mechanism for releasably engaging the valve anchor. The engagement mechanism can optionally be slidably coupled to the core member. The engagement mechanism can engage with a lock component, which can optionally be slidably coupled along the core member. Accordingly, in some embodiments, the engagement mechanism can be displaced or moved relative to the core member to releasably engage one or more features of the valve prosthesis. The engagement mechanism can permit one or more aspects of the valve anchor to radially expand while radially restricting expansion of or engaging with one or more adjacent aspects of the support frame.

For example, in some embodiments, the delivery system can engage one or more anchoring legs of the valve anchor with an engagement mechanism while being disengaged from one or more U-shaped member, anchoring member, valve clasper, sinus locator, valve positioner, or valve hangers of the valve anchor. The U-shaped members can each comprise a base portion that can be used to engage with certain aspects of the native valve structure, such as the aortic sinus, including the posterior aortic sinus, the left aortic sinus, and/or the right aortic sinus, of a native aortic valve. The base portions can have rounded or atraumatic shapes that permit the base portions to be expanded and fitted into respective sinuses of the valve. Accordingly, in some embodiments, the delivery system can engage one or more anchoring legs of the valve anchor while the base portions of the U-shaped members expand relative to the one or more anchoring legs, thereby allowing a clinician manipulate or move the base portions relative to the native valve structure to properly seat the valve anchor relative to the native valve structure.

In some embodiments, the base portions and the anchoring legs can extend in a longitudinal direction along the valve anchor. For example, the valve anchor can comprise three base portions and three anchoring legs. Each of the anchoring legs can be interconnected with and alternatingly interposed between respective base portions. First end sections of the anchoring legs can be interconnected with respective first end sections of the base portions. Further, second end sections of the anchoring legs can be releasably couplable to the delivery system using the engagement mechanism while second end sections of the U-shaped members (or base portions) can move independently of the second end sections of the anchoring legs (i.e., the second end sections of the anchoring legs may be coupled to the delivery system and the base portions of the U-shaped members can expand relative to the engaged second end sections of the anchoring legs).

Optionally, in some embodiments, the second end sections or base portions of the U-shaped members can be maintained in a compressed configuration using a sheath. For example, the sheath can be slidably positioned over the valve anchor and be retractable in order to permit the U-shaped members of the valve anchor to expand relative to the anchoring legs. Thereafter, the clinician can maneuver the base portions of the U-shaped members into position relative to the native valve structure. Once the base portions are properly positioned relative to the native valve structure (e.g., at a desired final position), the anchoring legs can be disengaged, thereby permitting the valve anchor to fully expand and be released from the delivery system. Once the valve anchor is seated or positioned relative to the native valve structure, the support frame can be positioned longitudinally within the lumen of the valve anchor, expanded, and released into engagement with the valve anchor. Other features and steps of the delivery system, the valve anchor, and methods of assembling and delivering the valve prosthesis are discussed further herein.

In accordance with some embodiments, the engagement mechanism can comprise a pin assembly. The pin assembly can include (i) a tubular component having current proximal and distal sections, and (ii) at least one pin coupled to the distal section. The pin can extend proximally from the distal section toward the proximal section and be radially spaced apart from the tubular component.

In some embodiments, the lock component can include at least one lock aperture (i) proximal to the tubular component distal section and (ii) configured to permit the at least one pin to extend therethrough.

Optionally, the valve anchor can include at least one anchoring leg. The anchoring leg can have a coupling portion with a connection aperture disposed therethrough to permit the engagement mechanism to engage the anchoring leg.

For example, in an engaged configuration, the tubular component distal section can be axially spaced apart from the lock component at a first distance to permit the at least one pin to extend through the connection aperture of the anchoring leg and the lock component lock aperture to interconnect the valve anchor leg with the engagement mechanism. Thus, in the engaged position, the anchoring leg can be engaged with the pin and interposed between the tubular component distal section and the lock component. In a released configuration, the tubular component distal section can be axially spaced apart from the lock component at a second distance, greater than the first distance, to position or release the at least one pin outside of the lock aperture to permit the anchoring leg to disengage from the at least one pin.

In accordance with some embodiments, methods for delivering a valve prosthesis to a target location in a vessel of a subject can include introducing a delivery system into the vessel to position a valve anchor at the target location. A sheath of the delivery system can be proximally retracted to permit the U-shaped members of the valve anchor to expand at the target location for positioning the valve anchor relative to the native valve structure. Once the base portions of the U-shaped members are engaged or seated within respective valve sinuses, for example, the anchoring legs of the valve anchor can be released to permit the valve anchor to fully expand within the native valve structure. Thereafter, a support frame of the valve prosthesis can be positioned within a lumen of the valve anchor, expanded, and engaged with the valve anchor. The delivery system can thereafter be removed from the patient.

Optionally, the valve anchor can be released by disengaging an engagement mechanism of the delivery system. For example, the engagement mechanism can comprise a pin assembly that engages with one or more anchoring legs of the valve anchor. The pin assembly can comprise a lock pin carrier that is coupled to a plurality of pins. In order to disengage the engagement mechanism, the lock pin carrier can be contacted by a lock activator in order to move the lock pin carrier relative to the anchoring legs in order to slide the pins out of engagement with the anchoring legs. The lock pin carrier can slide along and relative to a core member of the delivery system.

In some embodiments, the delivery system can comprise a nose cone having an engagement area and a plurality of apertures through which the pins can extend to permit the anchoring legs of the valve anchor to be engaged and restrained within the engagement area.

Optionally, the lock pin carrier can be at least partially disposed within a cavity of the nose cone and slide there within in order to move the pins into or out of the engagement area. For example, when the lock activator contacts the lock pin carrier, the lock pin carrier can be distally advanced relative to the engagement area of the nose cone, thereby withdrawing the pins from the engagement area and disengaging the pins from the anchoring legs of the valve anchor.

Accordingly, various embodiments can be provided in which movement of the engagement mechanism can cause disengagement of the delivery system from the anchoring legs of the valve anchor, thereby permitting release of the valve anchor from the delivery system.

Additional embodiments of the present devices and methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded or omitted from any embodiment of the present disclosure. Additional aspects and advantages of the present disclosure are set forth in the following description and claims, particularly when considered in conjunction with the accompanying examples and drawings.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

Certain features of valve prostheses, delivery devices, actuation handles, other devices, systems, and methods which can be implemented with the valve prostheses, delivery devices, actuation handles, other devices, systems, and methods discussed in the present disclosure, can implement features of and/or be used in combination with other features of valve prostheses, delivery devices, actuation handles, other devices, systems, and methods described for example in International Application No. PCT/US2019/012406, entitled HEART VALVE PROSTHESIS, filed on Jan. 4, 2019, by Ji Zhang, Brandon G. Walsh, Cheng Yong Yang, Jinhua Zhu, and Dennis Michael McMahon, and in International Application No. PCT/US2019/012408, entitled PROSTHETIC HEART VALVE DELIVERY SYSTEM, filed on Jan. 4, 2019, by Ji Zhang, Brandon G. Walsh, and Cheng Yong Yang, the entirety of each of which is incorporated herein by reference.

It is to be understood that both the foregoing general description and the following detailed description are exemplary and explanatory and are intended to provide further explanation of the subject technology.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 6A illustrates the support frame and the valve anchor housed in a compact state within a sheath of the delivery system of FIG. 2, according to some embodiments.

FIG. 6B illustrates the valve anchor in an expanded configuration, partially released from the sheath and engaged with the engagement mechanism, which is in a pre-released configuration, according to some embodiments.

FIG. 6C illustrates the distal advancement of the support frame and a pusher component of the engagement mechanism to initiate disengagement of the valve anchor from the engagement device, according to some embodiments.

FIG. 6D illustrates the valve anchor and the engagement mechanism in a released configuration, prior to release of the support frame from the sheath of the delivery system, according to some embodiments.

FIG. 6E illustrates the sheath being proximally retracted to permit the valve prosthesis to begin expansion, according to some embodiments.

FIG. 6F illustrates the valve prosthesis fully expanded within the valve anchor, according to some embodiments.

DETAILED DESCRIPTION

Figure 1:
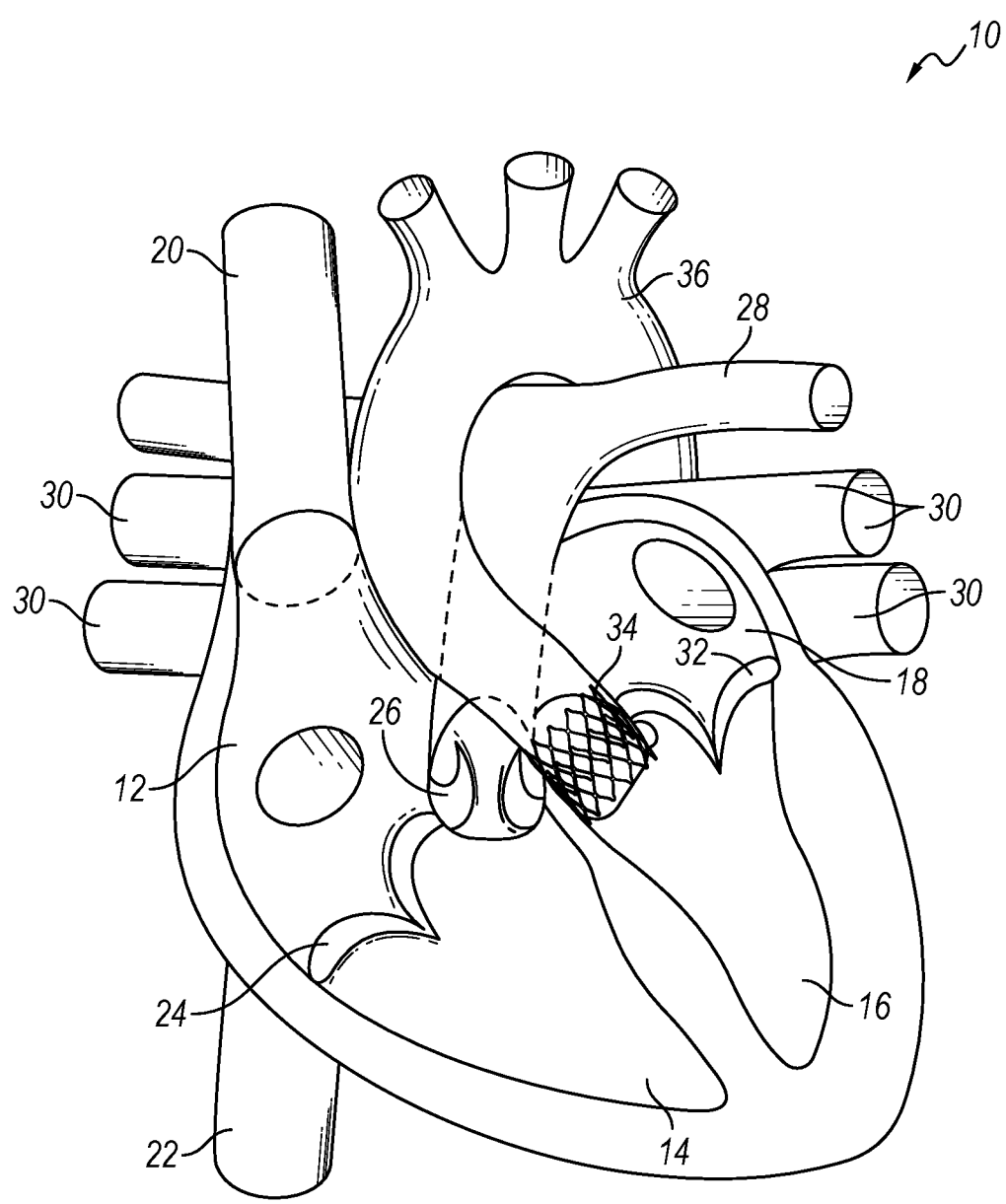
FIG. 1 illustrates a cross-sectional view of a human heart, and in particular, the implantation of an aortic valve prosthesis into a native valve structure of the heart, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present disclosure sets forth specific details of various embodiments, it will be appreciated that the description is illustrative only and should not be construed in any way as limiting. Additionally, it is contemplated that although particular embodiments of the present disclosure may be disclosed or shown in the context of mitral valve prostheses, such embodiments may be used in other cardiac valve prosthesis applications. Furthermore, various applications of such embodiments and modifications thereto, which may occur to those who are skilled in the art, are also encompassed by the general concepts described herein.

As with all cardiac valves, a healthy aortic valve will open to allow blood flow and close to prevent backflow of blood. However, disease and dysfunction of the valve can result in regurgitation or decreased blood flow. In such cases, a replacement valve prosthesis must be used to perform the functions of a healthy aortic valve.

However, there are numerous challenges in providing a replacement valve prosthesis. For example, in order to overcome the problem of regurgitation or decreased blood flow, a suitable replacement valve prosthesis must provide an acceptable seal and anchoring against the native valve tissue when positioned and released against the native valve structure, such as the native valve annulus. Further, the architecture of the aortic valve annulus also creates a challenge in the design of an aortic valve prosthesis. Indeed, the aortic valve prosthesis must conform to the unique anatomical structure of the aortic valve and remain anchored in the presence of the continuous contractions of a functioning heart.

The present disclosure describes systems, devices, and methods for implanting an aortic valve prosthesis using a minimally invasive surgical technique. The systems accommodate the complex structure of the aortic valve to ensure that the implanted valve prosthesis is properly positioned and securely maintained in place after implantation. Further, some embodiments also provide an aortic valve prosthesis delivery system that can comprise an aortic valve prosthesis.

The valve prosthesis can comprise an expandable valve anchor, a support frame that can be coupled to the valve anchor, and a plurality of valve leaflets coupled to the support frame. The implant can have a plurality of prosthetic valve leaflets attached to an internal surface thereof that can mimic the function of a native aortic valve. The implant and valve anchor can have a compact configuration for delivery to a diseased valve, and an unfolded or expanded configuration upon release and implantation in the diseased valve annulus. Moreover, in some embodiments, the implant and the valve anchor can be positioned relative to each other to minimize the diameter of the valve component during delivery.

Further, in some embodiments, the implant can be flexibly coupled to the valve anchor to provide efficient positioning of both the valve anchor and the implant. For example, the implant and the valve anchor can be connected by a flexible element such that prior to releasing and expanding the valve component in the heart or native valve structure, the implant and the valve anchor can be longitudinally or rotationally displaced relative to one another. Further, the implant and the valve anchor can expand from a compact state to an expanded state, and in some embodiments, independently of each other.

FIG. 1 illustrates a cross-sectional view of a human heart in which an aortic valve prosthesis has been implanted in a native valve structure of the heart. The heart 10 can comprise a right atrium 12, a right ventricle 14, a left ventricle 16, and a left atrium 18. Oxygen-depleted blood enters the right atrium 12 through the superior and inferior vena cava 20, 22. The oxygen-depleted blood is pumped from the right atrium, through a tricuspid valve 24, which separates the right atrium 12 from the right ventricle 14, and into the right ventricle 14. The right ventricle 14 then pumps the oxygen-depleted blood through a pulmonary valve 26 and into pulmonary arteries 28 that direct the oxygen-depleted blood to the lungs for oxygen transfer to the oxygen-depleted blood. Thereafter, oxygen-rich blood is transported from the lungs through pulmonary veins 30 to the left atrium 18. The oxygen-rich blood is pumped from the left atrium 18 through a mitral valve 32 and into the left ventricle 16. The left ventricle 16 then pumps the oxygen-rich blood through an aortic valve 34 and into the aorta 36. The oxygen-rich blood is carried by the aorta to a series of arteries that transport the blood to various organs in the body.

Implantation of a prosthetic aortic valve via a minimally invasive transcatheter approach may be accomplished, e.g., through the femoral artery and aortic arch into the left atrium or through the femoral vein and inferior vena cava by way of a transseptal punch. The aortic valve, between the left atrium and left ventricle, may be the most difficult valve to repair percutaneously because it can be difficult to reach. Although the aortic valve can be reached via the left ventricle and mitral valve, manipulation of catheters that have to make two approximately 180° turns is cumbersome. However, as discussed herein, various embodiments are provided that allow a clinician to overcome these disadvantages and effectively deliver a prosthetic valve to a target location in the heart.

Delivery Systems for the Valve Prosthesis

The present disclosure provides devices, systems, and methods for valve replacement, preferably using a minimally invasive surgical technique. While the systems and methods will have application in a number of different vessels in various parts of the body, they are particularly well suited for replacement of a malfunctioning cardiac valve, and in particular an aortic valve. The systems and methods will also have application in other malfunctioning cardiac valves, e.g., a pulmonary valve or a mitral valve.

The systems and methods disclosed herein can be particularly advantageous in their ability to provide a more flexible prosthetic heart valve delivery system, ensure accurate and precise placement of the prosthetic heart valve or valve prosthesis with reduced reliance on imaging, and provide additional anchoring of the valve prosthesis, reducing the incidence of valve migration.

Another advantage of the systems and methods disclosed herein is the ability to deliver and implant the valve prosthesis through the aorta, which has a smaller diameter than the inferior vena cava, through which surgeons typically proceed to access the heart.

The present disclosure also provides improved systems and methods for implanting a prosthetic heart valve. In particular, improved minimally invasive methods and systems are provided for retrograde implantation of expansible prosthetic heart valves within or adjacent a valved anatomic site within the heart. In particular, the improved prosthetic heart valve delivery systems and methods of the present disclosure provide more flexibility in the valve replacement procedure, ensure accurate and precise placement of the prosthetic heart valve with reduced reliance on imaging, and provide additional anchoring of the prosthetic valve, reducing the incidence of valve migration or misalignment.

Various embodiments of the disclosure are directed to a delivery system capable of maneuvering tight turns, and including a compactly configured valve prosthesis, which can comprise a valve anchor, a support frame that can be coupled to the valve anchor, and an engagement mechanism for releasable engaging the valve anchor. In the configuration of the delivery system 100, the valve anchor and support frame are delivered to a target location in a collapsed configuration serially (or longitudinally spaced relative to each other), rather than concentrically positioned relative to one another, thereby minimizing the outer profile or diameter of valve prosthesis and that of delivery system during delivery.

Various embodiments will now be described more fully hereinafter. Such embodiments may, however, be embodied in many different forms and should not be construed as limited to the embodiments set forth herein; rather, these embodiments are provided so that this disclosure will be thorough and complete, and will fully convey its scope to those skilled in the art. Thus, one or more features shown or otherwise disclosed in an embodiment herein may be interchangeably used or incorporated into another embodiment that may not expressly show or disclose such feature(s). Further, one or more features shown or otherwise disclosed for an embodiment herein may be excluded from such embodiment, unless expressly indicated, using skill in the art.

The valve prosthesis delivery system described herein thus facilitates delivery of a valve prosthesis to the heart while minimizing trauma or damage to the vessels and tissues of a patient. The various embodiments described herein provide a means for both pushing and pulling the valve prosthesis delivery system through the tight turns presented by the heart chambers. It is noted that for the purposes of describing the disclosed systems and methods, the term "proximal" refers to a relative position closer to a control unit whereas the term "distal" refers to a relative position further away from a control unit.

Figure 2:
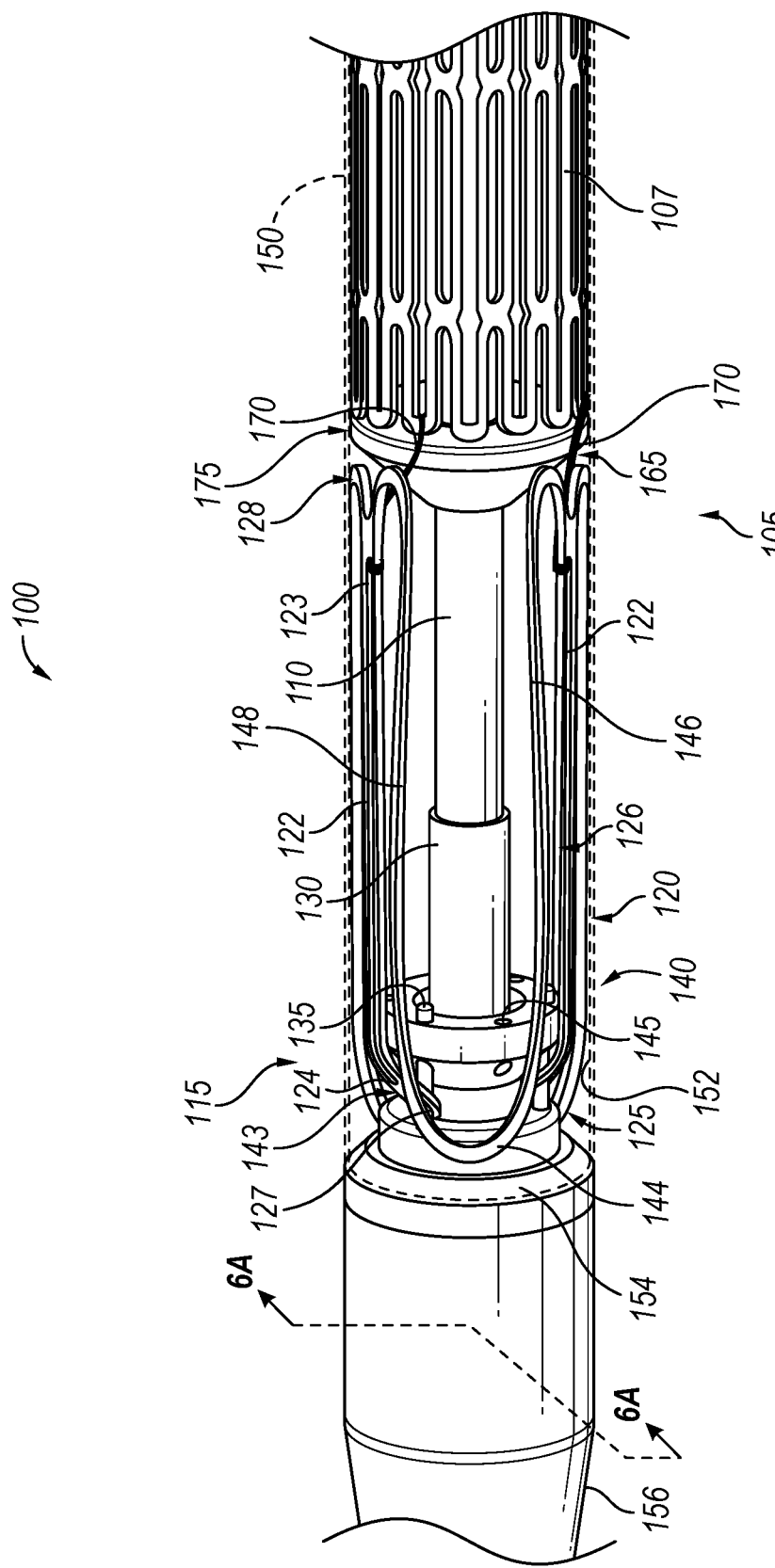
FIG. 2 illustrates a delivery system in a delivery configuration for delivering the valve prosthesis, including a radially expandable valve anchor and a support frame, using an engagement mechanism for releasable engaging the expandable valve anchor, according to some embodiments.

FIG. 2 illustrates a valve prosthesis delivery system 100 that can support and deliver a valve prosthesis 105. As shown, the valve prosthesis 105 can comprise a support frame 107 and a valve anchor 120. In accordance with some embodiments, the delivery system 100 may include a core member 110 and an engagement mechanism 115 that can be configured for releasably engaging the valve anchor 120 relative to the core member 110. Further, the delivery system 100 can also comprise a sheath 150 that can extend distally to cover the support frame 107 and the valve anchor 120. The sheath 150 can maintain the support frame 107 and the valve anchor 120 in a compressed configuration during delivery of the system 100 to the target location. When positioned at the target location, the clinician can proximally retract the sheath 150 in order to permit the support frame 107 to begin expanding. Thereafter, additional actuation of the engagement mechanism 115 and further proximal retraction of the sheath 150 can enable a clinician to release the valve prosthesis 105 at the target location.

In some embodiments, the engagement mechanism 115 may include a pin assembly 125 slidably coupled to the core member 110 and a lock component 140. Together, the pin assembly 125 and the lock component 140 can engage one or more structures of the valve anchor 120 and, when released by the clinician, can disengage from the valve anchor 120 to permit the valve anchor 120 to fully expand or be released at the target location. In this manner, the clinician can precisely control the release of the valve anchor 120 from the delivery system 100.

As illustrated in FIG. 2, the valve anchor 120 may be positioned serially with a support frame 107 of the valve prosthesis 105. Both the support frame 107 and the valve anchor 120 can be made from a shape memory material such that they can be compressed to a radius which allows delivery through, for example, arteries and veins, then expanded as needed for expansion and placement of the valve prosthesis 105 in a desired position.

Thus, although the support frame 107 and/or the valve anchor 120 can optionally be balloon-expandable or be further expandable using a balloon, the embodiment illustrated in FIG. 2 is configured such that the support frame 107 or the valve anchor 120 self-expand when the sheath 150 is proximally retracted to position in which the sheath 150 does not longitudinally overlap the respective one of the frame 107 or the valve anchor 120.

For example, the support frame 107 and/or the valve anchor 120 can comprise a braided frame, a wire frame, or a laser-cut frame, as shown in FIG. 2. In some embodiments, the support frame 107 and/or the valve anchor 120 can comprise a shape-memory metal, which can change shape at a designated temperature or temperature range or by inducing stress. Alternatively, the self-expanding frames can include those having a spring-bias. The material from which either the support frame 107 and/or the valve anchor 120 is fabricated can allow the support frame 107 and/or the valve anchor 120 to automatically expand to its functional size and shape when deployed but also allows the support frame 107 and/or the valve anchor 120 to be radially compressed to a smaller profile for delivery through the patient's vasculature. Examples of suitable materials for self-expanding components described herein (e.g., support frames, valve anchors, locking members) include, but are not limited to, medical grade stainless steel, titanium, nickel titanium alloys, tantalum, platinum alloys, niobium alloys, cobalt alloys, alginate, or combinations thereof. Shape memory alloys having superelastic properties generally made from ratios of nickel and titanium, commonly known as nitinol, are preferred materials. In some embodiments, self-expanding components described herein can include materials including, but not limited to shape memory plastics, polymers, and thermoplastic materials, which are inert in the body. In an alternative embodiment, either the support frame 107 and/or the valve anchor 120 is not self-expanding, and may be expanded, for example, using a balloon catheter as is well known in the art.

In some embodiments, the valve anchor 120 may be movably coupled to the support frame 107 such that the valve anchor 120 may be moved from a concentric position with the support frame 107 to a proximal or distal position from the support frame 107. During delivery of the valve prosthesis 105, it is advantageous to have the valve anchor 120 positioned serially from the support frame 107. This permits the radius of the system to be minimized, thus enabling the system to be advanced through small diameter vessels, for example, arteries, and veins. The distance from which the valve anchor 120 may be serially displaced from the support frame 107 is variable, such that the valve anchor 120 may be adjacent to the support frame 107, or potentially inches away from the support frame 107 during the delivery procedure. In some embodiments, the valve anchor 120 is physically fixed to the support frame, such as by welding or otherwise adhering.

The delivery system 100 can be configured such that components of the heart valve prosthesis to be advanced in series while still being movably connected, movably attached, flexibly connected, displaceably connected, linked, or coupled to each other, thereby minimizing a passing profile or cross section of the delivery system. The interconnection of components of the heart valve prosthesis can allow different degrees of motion and can be set into an engaged or retained position that provides a limited range of motion. In some embodiments, the engaged position can also provide a preset relative positioning of the components of the heart valve prosthesis to facilitate proper placement and release of the heart valve prosthesis. Additionally, some embodiments can provide a clinician with a high degree of control and enhance the maneuverability of the heart valve prosthesis when implanting the heart valve prosthesis at the target location.

In some embodiments, the valve anchor 120 can be coupled to the support frame 107 when the support frame 107 is in the compact configuration prior to delivery and expansion. In some embodiments, the valve anchor 120 is not fixed to the support frame 107. Further, the valve anchor 120 can be separate from the support frame 107 or formed separately from and later coupled to the support frame 107. Thus, although a least a portion of the valve anchor, e.g., the anchoring leg, may be in contact with or otherwise reversibly attached or connected to the support frame, no part of the valve anchor is fixed, e.g., welded or otherwise irreversibly adhered, to the support frame. Alternatively stated, the valve anchor, which may be in contact with or otherwise reversibly attached to the support frame, is not irreversibly fixed to the support frame.

Further, upon reaching the target location, the valve anchor 120 can be movably coupled to the support frame 107 in a manner that prevents the entire valve anchor 120 from being radially displaced from the support frame 107 when the valve anchor 120 is initially expanded. For example, portions of the valve anchor 120 can be radially displaced from the support frame during initial "landing" of the valve anchor 120 against the native valve structure at the target location. In some embodiments, the support frame 107 can be deployed or expanded within the native heart valve structure, and the valve anchor 120 can become sandwiched between the support frame and the native valve tissue, becoming at least partially, and possibly fully, immobilized (as shown, for example, in FIGS. 7E and 7F). The valve anchor 120 can function to hold the expanded support frame 107 in place within the native valve structure.

In some embodiments, the valve anchor 120 can comprise at least one U-shaped member, anchoring member, valve clasper, sinus locator, valve positioner, or valve hanger 126 and at least one anchoring leg 122. The U-shaped member 126 and the anchoring leg 122 can extend along a longitudinal axis of the valve anchor 120. As illustrated in FIG. 2, the valve anchor 120 can comprise a plurality of U-shaped members 126, such as three U-shaped members 126, but can have fewer or more.

The U-shaped members 126 can be coupled to the anchoring legs 122 at peak portions or apices 128 of the valve anchor 120. Further, adjacent U-shaped members 126 can be coupled to each other at a respective apex 128. The U-shaped members 126 can each comprise first and second legs 146, 148 that meet or join at a base portion 144 thereof. The base portions 144 of the U-shaped members 126 can be configured to engage with or fit inside the posterior aortic sinus, the left aortic sinus, and the right aortic sinus of a native aortic valve. The first and second legs 146, 148 of the adjacent U-shaped members 126 can be interconnected at the peak portions 128 thereof.

Referring now to FIGS. 2 and 6A-6F, the valve anchor 120 may include at least one anchoring leg 122. The anchoring leg 122 can include a coupling portion 124 having a connector or connection aperture 127. The connector can comprise structures, such as slots or holes extending through the coupling portion 124.

In some embodiments, the anchoring leg 122 of the valve anchor 120 is positioned approximately parallel relative to the longitudinal axis of the support frame 107 and is attached to U-shaped member 126 at an apex 128. As used herein, the apex 128 may be a vertex where the U-shaped member(s) 126 joins with the anchoring leg 122. In some embodiments, two U-shaped members 126 may curve to join the anchoring leg 122 at the vertex or apex 128. In some embodiments, the vertices of the valve anchor 120 may be configured such that two anchoring legs 122 extend approximately parallel relative to each other. In some embodiments, the valve anchor 120 includes at least two U-shaped members 126 and two anchoring legs 122.

Each of the first or proximal ends of the two anchoring legs 122 are joined to the U-shaped member 126. In additional embodiments, as illustrated in FIG. 2, the second or distal end of one or more of the anchoring legs 122 terminates in a coupling portion 124. That is, the coupling portion 124 of the valve anchor 120 is positioned at an end portion of the valve anchor anchoring leg 122. The coupling portion 124 may be made of a shape memory alloy such as nitinol. For some applications, the coupling portion 124 may be oriented parallel relative to a longitudinal axis of the valve prosthesis 105, while for other applications, the coupling portion 124 may be oriented to form an angle with respect to the longitudinal axis.

For example, the coupling portion 124 may be approximately parallel relative to the longitudinal axis of the support frame 107 in the compact position and/or when the valve prosthesis 105 is encased in a sheath 150. Alternatively, as illustrated in FIG. 2, the coupling portion 124 may form an angle with respect to the longitudinal axis of the valve prosthesis 105 or the anchoring leg 122 when the valve prosthesis 105 is in an expanded condition. The detents can help to secure the valve anchor 120 to the support frame 107 after the valve prosthesis 105 is expanded in the native valve.

It will be appreciated by those with skill in the art that the shape of the base portion 144 joining the two anchoring legs 122 of the U-shaped member 126 is not limited to being a U-shaped or rounded. The base portion 144 may have other shapes including, but not limited to, rectangle, square, diamond, triangle, oval, circle, or a combination of these shapes. The base portion 144 may be of any shape that allows it to engage and/or rest adjacent to the commissure of the native valve leaflets 190.

In some embodiments, the valve anchor 120 may comprise a plurality of U-shaped members 126 coupled to the support frame 107. That is, the delivery system 100 may include, but is not limited to, two, three, four, five, or more plurality of U-shaped members 126, to accommodate different valve replacement procedures or according to the anatomical structure of the native valve that is to be replaced. In the various embodiments disclosed in the figures, the number of plurality of U-shaped members 126 in the valve prosthesis is three.

Additionally, in accordance with some embodiments, the valve prosthesis 105 can be configured such that the support frame 107 is coupled to the valve anchor 120. For example, the valve prosthesis 105 can comprise at least one suture 170 that couples the support frame 107 to the valve anchor. In some embodiments, a distal end portion of the support frame 107 can be coupled to the valve anchor 120 via the suture 170. The portion of the suture 170 that attaches to the valve anchor 120 can be coupled to and anchoring leg 122 of the valve anchor 120. In accordance with some embodiments, the anchoring leg 122 can comprise a longitudinal slot 123 that extends along the length of the anchoring leg. The suture 170 can loop into the slot 123 and be coupled with the anchoring leg 122. This can enable the suture 170 to slide along the length of the slot 123 during expansion of the valve prosthesis 105, as discussed further herein.

Figure 3A:
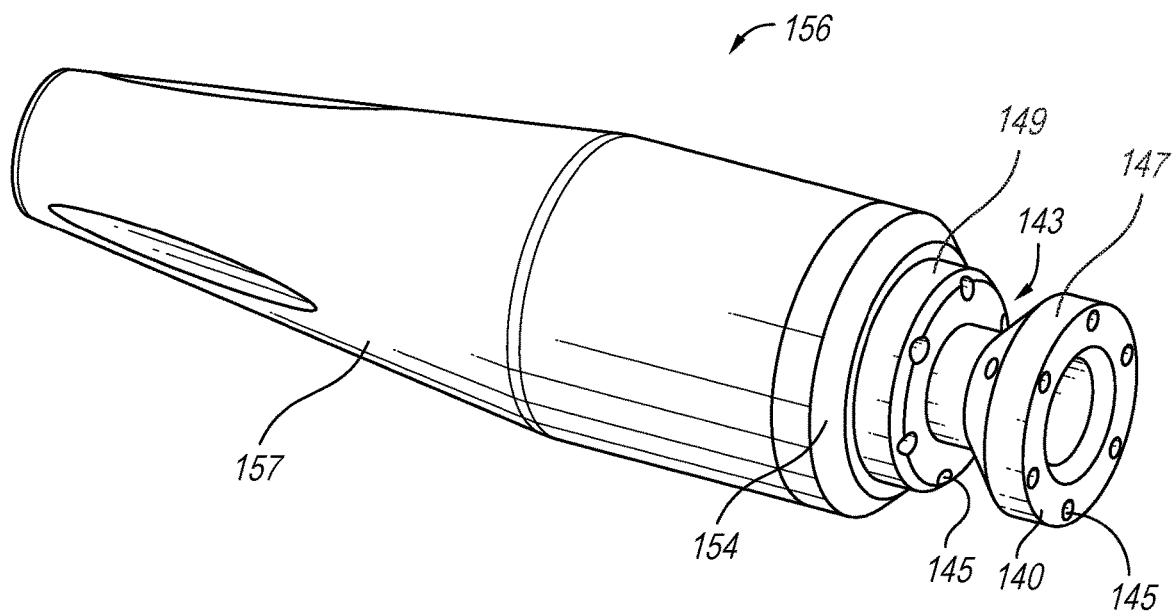
FIG. 3A is an illustration of a nose cone of the valve anchor of the delivery system of FIG. 2, according to some embodiments.
Figure 3B:
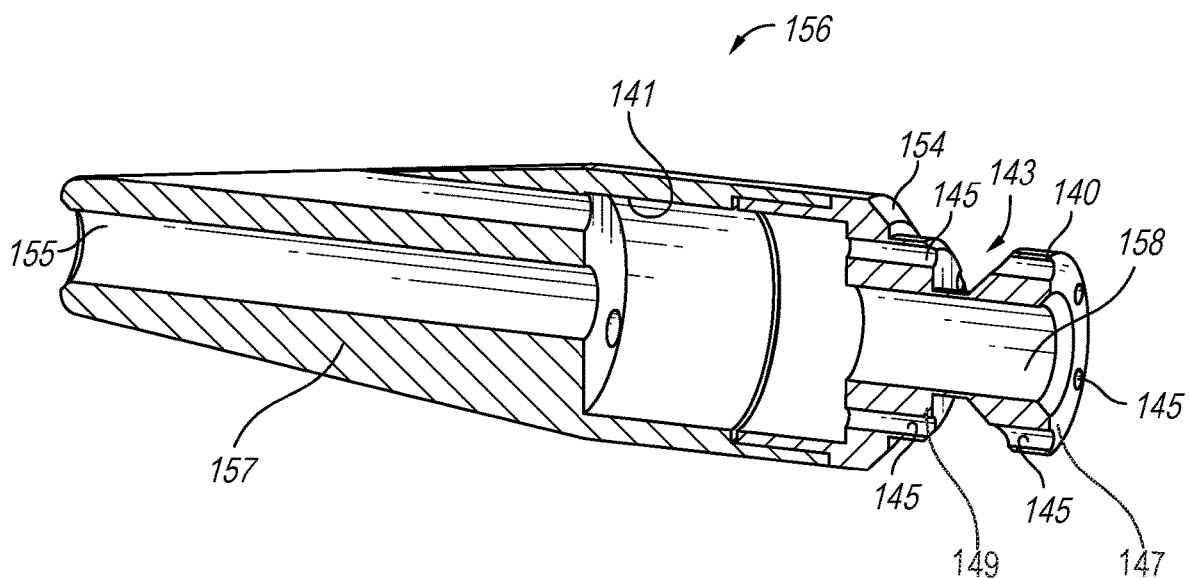
FIG. 3B illustrates a cross-sectional view of the nose cone of the valve of FIG. 3, according to some embodiments.

FIGS. 3A and 3B are illustrations of perspective and cross-sectional views of an embodiment of a nose cone 156 of the valve anchor delivery system 100 of FIG. 2. As illustrated in FIGS. 2, 3A, and 3B, the delivery system 100 may include a nose cone 156 at a distal end thereof. The nose cone 156 may have a substantially tubular and/or conical profile that tapers towards a distal end of the nose cone 156. Further, the nose cone 156 can comprise a lock component 140 and a cavity 141. In some embodiments, the nose cone 156 can interact as part of the engagement mechanism 115, to permit the lock component 140 and the pin assembly 125 to engage the valve anchor 120.

In accordance with some embodiments, the nose cone 156 may be configured to be coupled to or mate with a distal end of the valve sheath 150 in order to reduce any seam along the outer surface of the delivery system 100 between the nose cone 156 and the sheath 150. The mating engagement between the nose cone 156 and the sheath 150 can thereby provide a smooth, continuous outer surface of the delivery system 100.

For example, the nose cone 156 may include a radial depression 154 against which the distal end of the valve sheath 150 can be positioned in a delivery configuration. The radial depression 154 can permit at least a portion of the nose cone 156, including the lock component 140, to be inserted into a lumen 152 of the valve sheath 150 to detachably couple the nose cone 156 to the valve sheath 150. Although the radial depression 154 is illustrated as having a generally conical profile, the radial depression 154 can also comprise a stepped profile in which the outer diameter of the nose cone 156 steps down from a diameter approximately equal to an outer diameter of the sheath 150 to a diameter that is approximately equal to an inner diameter of the sheath 150. In this manner, the nose cone 156 can fit inside of the sheath lumen and engage with the sheath 150 while both having a common or approximately equal outer diameter.

In some embodiments, the lock component 140 can be integrally formed with nose cone 156. However, in some embodiments, as illustrated in FIGS. 3A and 3B, the nose cone 156 can be an assembly of components, including a distal cone component 157 and the lock component 140. The lock component 140 can comprise an aperture 158 through which the pin assembly may be engaged or moved by the pusher component, as discussed below.

For example, as illustrated in FIG. 3B, a proximal end portion of the distal cone component 157 can be coupled with a distal end portion of the lock component 140 by welding, frictional engagement, or other adhesive means. Further, the distal cone component 157 and the lock component 140 can collectively form the cavity 141. In some embodiments, both the distal cone component 157 and the lock component 140 can comprise inner cavities that combined to form the cavity 141 when the distal cone component 157 and the lock component 140 are coupled together. As discussed further herein, the cavity 141 can provide a volume in which the pin assembly 125 of the engagement mechanism can reciprocate.

The nose cone 156 may further include a channel or passageway 155 extending centrally along a longitudinal axis of the nose cone. The channel 155 may be configured to receive the core member 110 as the core member reciprocates proximally and distally along the longitudinal axis in order to cause a corresponding motion of the support frame 107 and the valve anchor 120.

In accordance with some embodiments, the lock component 140 may include at least one lock aperture 145. The lock aperture 145 may be disposed proximal to the cavity 141. In some embodiments, the pin assembly 125 can include a plurality of pins 135, and the lock component 140 can include a plurality of lock apertures 145, each corresponding to one of the plurality of pins 135.

Further, as illustrated, the lock component 140 can comprise an engagement region 143 interposed between a proximal flange 147 and a distal flange 149. The lock aperture 145 can extend through both the proximal flange 147 and the distal flange 149. The lock aperture 145 that extends through the distal flange 149 can extend into the cavity 141. Accordingly, a pin extending from the pin assembly 125 can pass through the distal flange 149, extend across the engagement region 143, and pass through the proximal flange 147. Thus, as illustrated and discussed further herein, a pin of the pin assembly 125 can be radially constrained by the lock aperture 145 extending through the distal flange 149 and the proximal flange 147 and engage with a portion of the valve anchor 120 that extends into the engagement region 143.

For example, as illustrated in FIGS. 6A-6F, the pin assembly 125 can reciprocate within the cavity 141 between an engaged configuration (shown in FIGS. 6A-6C) and a disengaged configuration (shown in FIGS. 6D-6F). When the pin assembly 125 moves from the engaged configuration to the disengaged configuration, pins 135 of the pin assembly 125 can slide out of engagement with the lock apertures 145 of the lock component 140. As such, the pins 135 can be distally advanced out of the engagement region 143 and received into the cavity 141 and the distal flange 149, thus disengaging with valve anchor 120 and permitting the valve anchor 120 to expand out of the engagement region 143.

As illustrated in FIGS. 6A-6C, the pin assembly 125 and the lock component 140 can engage the valve anchor 120 in an engaged configuration. Thus, after the sheath 150 has been proximally withdrawn to permit U-shaped members of the valve anchor 120 to expand radially, the valve anchor 120 remains engaged with the delivery system 100, thereby permitting the clinician to rotate, repositioning, or otherwise maneuver the U-shaped members of the valve anchor 120 into a desired position relative to the native valve structure.

Figure 4A:
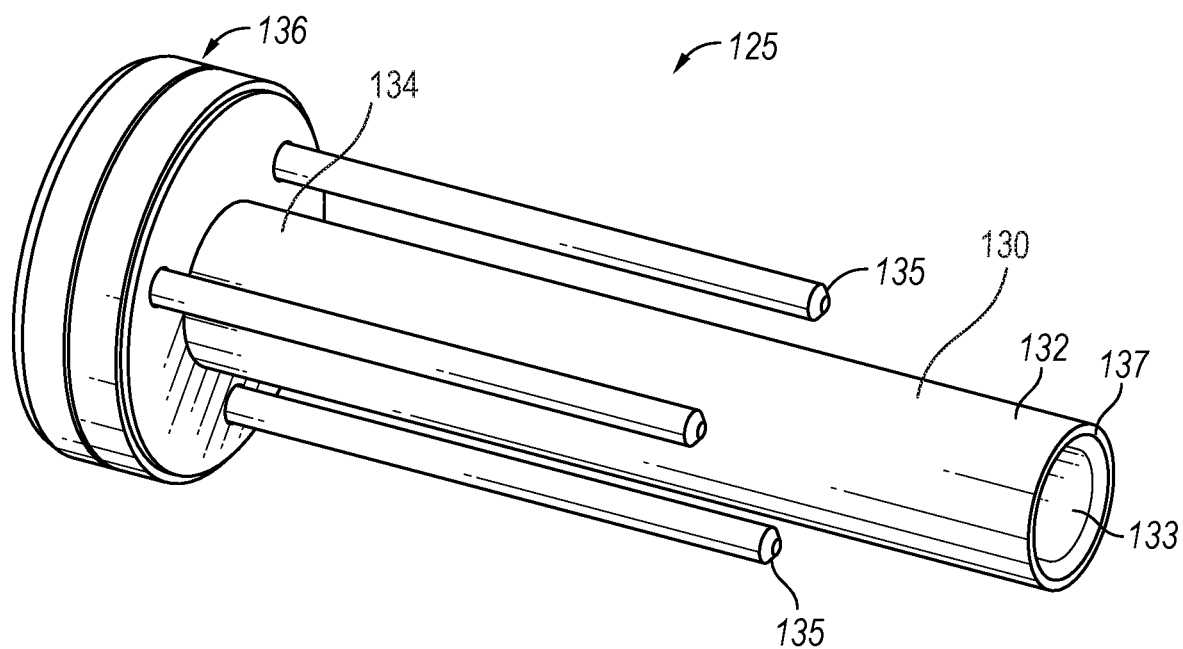
FIG. 4A illustrates a pin assembly of the delivery system of FIG. 2, according to some embodiments.
Figure 4B:
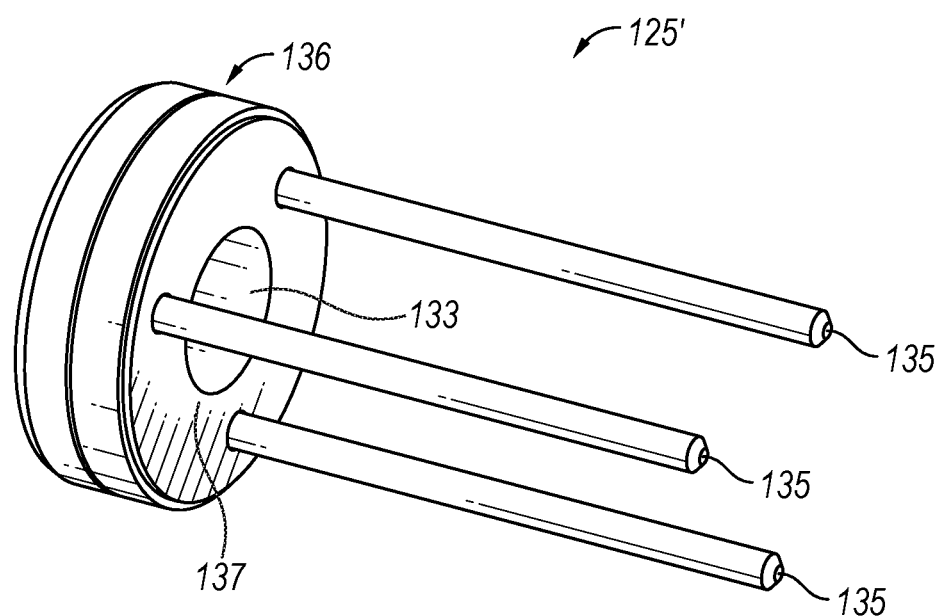
FIG. 4B illustrates an alternative pin assembly, according to some embodiments.

FIGS. 4A and 4B illustrate a pin assembly 125 and an alternative pin assembly 125', either of which can be used with the delivery system 100 of FIG. 2, according to some embodiments. As illustrated in the embodiment shown in FIG. 4A, the pin assembly 125 may comprise a tubular component 130 having a proximal section 132 and a distal section 134. Further, both pin assemblies 125, 125' can comprise an annular component, such as a piston member 136, and at least one pin 135 coupled to the annular component or piston member 136. The annular component can have the shape of a disc, a cylinder, a torus, or others that can be coupled to and at least partially surround the core member 110. The pin assembly 125 can also be configured such that the distal section 134 of the tubular component 130 is coupled to the piston member 136. The alternative pin assembly 125' can be identical to the pin assembly 125 of FIG. 4A in all respects except for the absence of the tubular component 130.

The pin assemblies 125, 125' can slide along the core member 110 of the delivery system 100. For example, the core member 110 can be configured to extend through the lumen 133 of the pin assembly 125. The lumen 133 can extend through both the tubular component 130 and the piston member 136.

An advantage of the pin assembly 125 may lie in the presence of the tubular component 130, which can assist in maintaining axial alignment of the piston member 136 and the pins 135 relative to the longitudinal axis of the delivery system 100 during use. However, in either embodiment of the pin assembly, the longitudinal extent of the lumen 133 through the piston member 136 can be of a sufficient length in order to prevent misalignment or wobbling of the piston member 136 relative to the core member 110. Accordingly, both pin assemblies 125, 125' can advantageously maintain the pins 135 in an alignment that is approximately parallel relative to the core member 110. In this manner, the pins 135 can slide smoothly out of engagement with the lock apertures 145 of the lock component 140. Further, proximal ends of the pins 135 can be advanced distally through the engagement region 143 sufficiently to permit the valve anchor 120 to disengage therefrom. Thus, in some embodiments, although the pins 135 may continue to extend into the engagement region 143, the valve anchor 120 may be able to disengage therefrom. However, in some embodiments, the proximal ends of the pins 135 may be fully received into the lock apertures 145 such that the pins 135 do not extend into the engagement region 143 in the disengaged configuration.

Although only one or two pins 135 may be used, the illustrated embodiments provide for three pins 135 to be used. The pins 135 extend proximally from the piston member 136 and can be radially spaced apart from the tubular component 130.

Optionally, in some embodiments, the piston member 136 can comprise two plates or discs that are coupled to each other. In such embodiments, the pins 135 may be positioned to extend through a proximal plate with distal end portions of the pins 135 being sandwiched between the proximal plate and a distal plate of the piston member 136, thereby engaging the distal end portions of the pins 135 therebetween.

For example, the distal end portions of the pins 135 may be bent at angles, as illustrated in FIGS. 6A-6F, and at least one of the two piston members 136 may have a groove formed therein to accommodate and hold the bent distal end portions of the pins 135 in a fixed position with respect to the pin assembly 125 when the proximal and distal plates of the piston member 136 are coupled together. Alternatively, however, the pins can be welded, mechanically fastened, or otherwise adhesively coupled to the piston member 136.

Accordingly, the piston member 136 and the pins 135 can slide along the core member 110 as a unit between engaged and disengaged positions, as discussed herein.

Figure 5A:
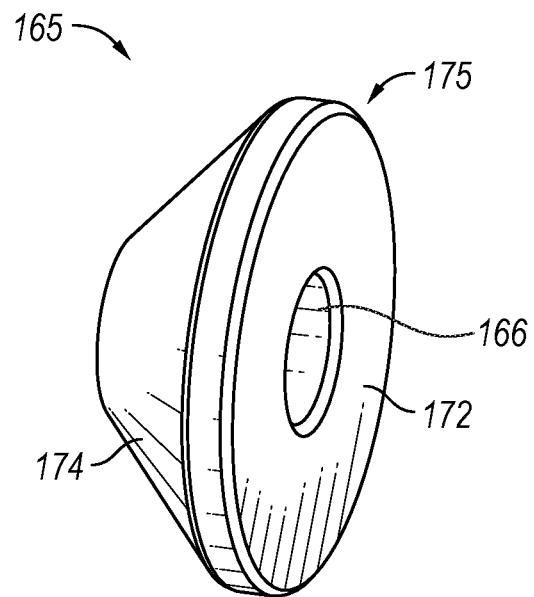
FIG. 5A illustrates a pusher component of the delivery system of FIG. 2, according to some embodiments.
Figure 5B:
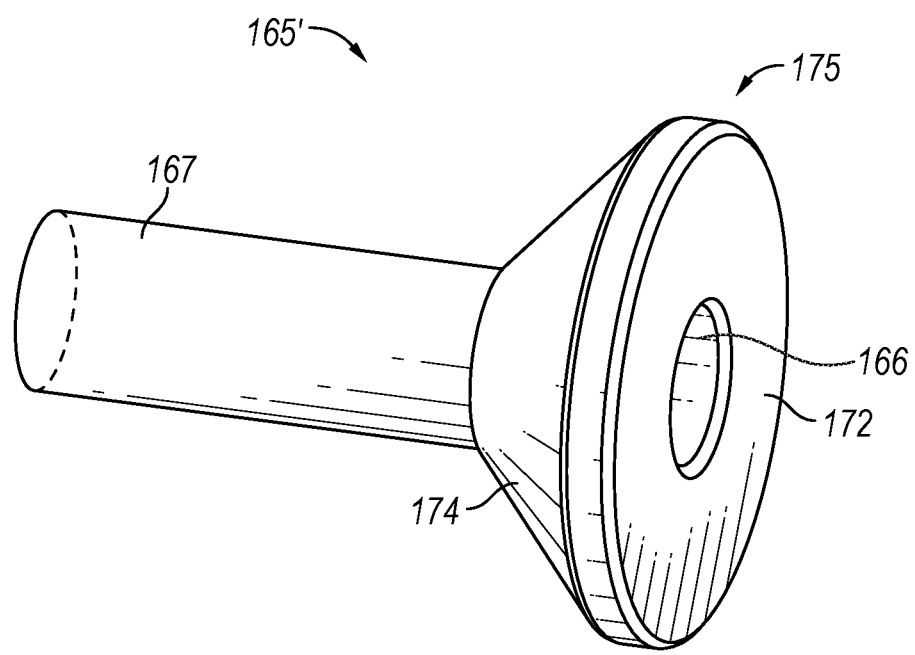
FIG. 5B illustrates an alternative pusher component, according to some embodiments.

FIGS. 5A and 5B illustrate a pusher component 165 and an alternative pusher component 165', either of which can be used with the delivery system 100 of FIG. 2, according to some embodiments. In some embodiments, the pusher component 165 can be used in combination with the pin assembly 125, shown in FIG. 4A.

The pusher component 165' can be used in combination with the pin assembly 125', shown in FIG. 4B. In the embodiment shown, whereas the pusher component 165 does not include an elongate shaft component that contacts against the pin assembly 125, the pusher component 165' may vary from the pusher component 165 by including a shaft component 167 that can extend through the aperture 158 of the lock component 140 of the nose cone 156. When used with the pin assembly 125', the shaft component 167 of the pusher component 165' can extend through or into the aperture 158 to facilitate movement and disengagement of the pin assembly 125'. However, these components 125, 125', 165, 165' can be interchanged or modified in any of the embodiments disclosed herein. Thus, in some embodiments, the pusher component 165 can be contacted against the tubular component 130 of the pusher component 165 extending through the aperture 158 of the lock component 140. However, in some embodiments, the shaft component 167 of the pusher component 165' can extend through the aperture 158 of the lock component 140 to contact against the pin assembly 125'.

As illustrated in FIGS. 5A and 5B, the pusher component 165 and the pusher component 165' may each comprise a lumen 166 through which the core member 110 can pass, thereby permitting the pusher component 165 and the pusher component 165' to be slidably disposed along the core member 110. As illustrated in the system views of FIGS. 6A-6F, the pusher component 165 (whether the pusher component 165 and the pusher component 165') can be disposed distally relative to the support frame 107. Eventually, as discussed below, the pusher component 165 can be contacted against the tubular component 130 of the pusher component 165, which extends through the aperture 158 of the lock component 140.

In accordance with some embodiments, the pusher component 165 can have an outer diameter or profile that is about equal to a compressed diameter of the support frame 107. Thus, the pusher component 165 and the support frame 107 can be received within the lumen of the sheath 150. Further, the distal end portion of the support frame 107 can abut or contact a proximal face 172 of the pusher component 165. As discussed further herein, some embodiments can permit the support frame 107 to be pressed distally against the proximal face 172 of the pusher component 165 in order to exert a distally directed force against the pusher component 165, which can then cause the pusher component 165 to contact the pin assembly 125 and cause disengagement of the pins 135 from the valve anchor 120.

In some embodiments, the pusher component 165 comprises a flange 175. As illustrated in FIG. 5A, the flange 175 may be a radial flange that defines the proximal face 172. Further, the pusher component 165 can comprise a distal face 174 having a generally sloped or conical profile. The conical profile of the distal face 174 can tend to allow the pusher component 165 to avoid catching or otherwise engaging with the valve anchor 120 during distal advancement of the pusher component through the valve anchor 120, as discussed below.

Although various mechanisms can be employed, in some embodiments, distal advancement of the pusher component 165 can be achieved by contacting the distal end of the support frame 107 against the proximal face 172 of the pusher component 165. For example, with reference to FIG. 6A, the delivery system 100 can comprise a pushing block 178 that is coupled to a pusher tube 179. The pusher tube 179 and the pushing block 178 can each comprise lumens through which the core member 110 can pass. The pusher tube 179 and the pushing block 178 can be slidably positioned along the core member 110. During the procedure, once the sheath 150 has been proximally retracted to a position approximately shown in FIG. 6B, the pusher tube 179 and the pushing block 178 can be distally advanced by the clinician along with the sheath 150, which can exert a distal force against the support frame 107 and the pusher component 165. This distally oriented force can urge the pusher component 165 toward a proximal contact face or area 137 of the pin assembly 125, 125', shown illustratively by the movement depicted from FIGS. 6B to 6C.

Accordingly, in some embodiments, the distal face 174 of the pusher component 165, 165' can contact the proximal contact face 137 of the pin assembly 125, 125' and urge the pin assembly 125, 125' in a distal direction relative to the lock component 140. In some embodiments, the tubular section can be coupled to either the pusher component or the pin assembly or to both. Movement of the pin assembly 125, 125' in the distal direction results in shifting of the engagement mechanism 115 from the engaged configuration (shown in FIG. 6C) to the released configuration (shown in FIG. 6D).

Accordance with some embodiments, the pusher tube 179 and the pushing block 178 can be actuated via a control unit (not shown) that can be operated by the clinician. The control unit can be communicatively coupled to the core member 110 and to the pusher tube 179 to allow the clinician to actuate or move the core member 110 relative to the pusher tube 179. In this manner, the pusher tube 179 can be distally advanced over the core member 110 in order to cause the pusher component 165 to contact the pin assembly 125 and cause the pin assembly 125 to move within the cavity 141 of the nose cone 156, thereby distally advancing the pins 135 through the engagement region 143.

In some embodiments, the control unit can be communicatively coupled to the pusher component 165 to selectively actuate the pusher component 165 without requiring interaction from the pusher block 178 and the support frame 107. For example, the pusher component 165 can be directly coupled to the pusher tube 179 in order to directly actuate the pusher component 165 to contact and urge the pin assembly 125 in the distal direction relative to the lock component 140. Similar to the embodiment illustrated in figures, such an embodiment can move the engagement mechanism 115 from the engaged configuration to the released configuration.

In some embodiments, the lumen 166 of the pusher component 165 can have an inner diameter that is smaller than an inner diameter of the tubular component 130 or the lumen 133 of the pin assembly 125. Such embodiments can thus allow the pusher component 165 to have a sufficient cross-sectional profile to allow the pusher component 165 to advance distally and contact and eventually urge or push the pin assembly 125 distally.

FIGS. 6A-6C illustrate the valve anchor 120 of the delivery system 100 in the engaged configuration. When the legs 122 of the valve anchor 120 are inserted into the engagement region 143 and locked in place via the engagement mechanism 115, this is referred to the engaged configuration (see FIGS. 6A-6C). In the engaged configuration, the pins 135 are positioned extending from the cavity 141 of the nose cone 156, through the connection aperture 126 of the valve anchor leg 122, and into and through the lock apertures 145 of the lock component 140 of nose cone 156. As such, in the engaged configuration, the at least one leg 122 of the valve anchor 120 is locked in engagement at a position between the lock component 140 of the nose cone 156 and the rest of the nose cone 156.

Further, FIG. 6A illustrates the valve prosthesis 105 and the valve anchor 120 housed in a compact state within the sheath 150 of the delivery system 100, according to some embodiments. When the delivery system 100 is initially introduced into the target location of the defective valve, the delivery system 100 is delivered in the compact state, as illustrated in FIG. 6A.

FIG. 6B illustrates the valve anchor 120 in an engaged configuration, but released from the sheath 150 of the delivery system 100 of FIG. 2, according to some embodiments. Once the delivery system 100 nears the target location, the sheath 150 of the delivery system 100 is proximally retracted relative to the core member 110 via, for example, a control unit including at least one controller or processor. Retraction of the sheath 150 from over the valve anchor 120 allows the valve anchor 120 to expand radially. The U-shaped members 126 can thereafter be guided and maneuvered into a desired position relative to the surrounding native valve structure, as discussed herein.

After the U-shaped members 126 are in a desired position relative to the surrounding native valve structure, the remainder of the valve anchor 120 can be released. FIG. 6C illustrates the first step and releasing the valve anchor 120. As shown, in some embodiments, the pusher block 178, the sheath 150, and the support frame 107 can be urged in a distal direction, thereby distally advancing the pusher component 165 towards the pin assembly 125 of the delivery system 100. This distal movement of the pusher component 165 into the lumen of the valve anchor 120 is possible because the valve anchor 120 has already expanded radially, despite being locked in the engaged configuration by the engagement mechanism 115. In the partially expanded position illustrated in FIG. 6C, the at least one U-shaped member 126 of the valve anchor 120 may extend radially from the anchoring leg 122 of the valve anchor 120 and the longitudinal axis of support frame 107.

As also illustrated in FIG. 6C, in the engaged configuration, the tubular component distal section 134 or a proximal surface of the piston member 136 is axially spaced apart from a proximal surface of the lock component 140 at a first distance D1. The first distance D1 is sufficient to permit the pins 135 to extend from the cavity 141 through the lock apertures 145 and the engagement region 143; as such, the pins 135 can extend through the leg connection aperture 127 of the valve anchor 120 and the lock component lock aperture 145 to interconnect the valve anchor anchoring leg 122 with the engagement mechanism 115. For example, the first distance D1 may be between about 1 mm and about 20 mm, between about 2 mm and about 15 mm, between about 4 mm and about 12 mm, between about 6 mm and about 10 mm, between about 8 mm and about 10 mm, or about 2 mm, about 2 mm, about 4 mm, about 6 mm, about 8 mm, about 10 mm, about 12 mm, about 14 mm, about 16 mm, about 18 mm, about 20 mm, about 22 mm, about 24 mm, about 26 mm, about 28 mm, about 30 mm, about 35 mm, or about 40 mm.

As the pusher component 165 is urged distally, the pusher component contacts the pin assembly 125 and begins to urge the pin assembly 125 distally through the cavity 141. As this happens, the pins 135 slide distally through the engagement region 143, eventually permitting the anchoring legs 122 to disengage from the pins 135 and permitting the valve anchor 120 to assume a released configuration. FIG. 6D is an illustration of the valve anchor 120 in a released configuration.

Referring still to FIG. 6D, in the released configuration, the tubular component distal section 134 or the proximal surface of the piston member 136 can be axially spaced apart from the proximal surface of the lock component 140 at a second distance D2, which is greater than the first distance D1. The second distance D2 is sufficient to position the pins 135 outside of the lock aperture 145 to permit the valve anchor leg 122 to disengage from the pins 135 of the pin assembly 135. For example, the second distance D2 may be between about 1 mm and about 20 mm, between about 2 mm and about 15 mm, between about 4 mm and about 12 mm, between about 6 mm and about 10 mm, between about 8 mm and about 10 mm, or about 2 mm, about 2 mm, about 4 mm, about 6 mm, about 8 mm, about 10 mm, about 12 mm, about 14 mm, about 16 mm, about 18 mm, about 20 mm, about 22 mm, about 24 mm, about 26 mm, about 28 mm, about 30 mm, about 35 mm, or about 40 mm.

In operation, as the pin assembly 125 is advanced distally, the pins 135 are displaced a distance corresponding to the difference between D2 and D1, thereby releasing the valve anchor 120 from engagement with the pin assembly 125, and allowing the valve anchor 120 to radially expand in preparation for positioning the support frame 107 therewithin.

As illustrated in FIG. 6D, after the valve anchor 120 has been released from the delivery system 100, the support frame 107 continues to be housed within the sheath 150 of the delivery system 100. However, after the longitudinal or axial position of the support frame 107 has been adjusted to be centered or otherwise properly positioned within the lumen of the valve anchor 120, the clinician can thereafter initiate release and expansion of the support frame 107 within the lumen of the valve anchor 120. As part of this adjustment for positioning process, the clinician may distally advance the support frame 107. In some implementations of the method, the clinician may advance the support frame 107 to a position longitudinally distal to the valve anchor 120 and thereafter proximally retract the support frame 107. Such a motion may ensure that the native valve leaflets are drawn upwardly between a space between the valve anchor 120 and the support frame 107. Thereafter, the expansion and release of the support frame 107 can be initiated by the clinician, as discussed further below.

Expansion and release of the support frame 107 can be initiated, as illustrated in FIG. 6E. FIG. 6E illustrates the sheath 150 being proximally retracted to expose and permit initial expansion of the support frame 107. FIG. 6F illustrates the sheath 150 being further retracted to permit the support frame 107 to be fully expanded within the valve anchor 120. In some embodiments, further retraction of the sheath 150 causes the valve prosthesis 105 to be completely exposed, thereby allowing the valve prosthesis to expand radially within the valve anchor 120. However, in some embodiments, the outward force of the self-expanding support frame 107 can cause the support frame 107 to spring open after the sheath 150 has been partially proximally withdrawn (i.e., reaching a position distal to that illustrated in FIG. 6F).

Methods for Operating and Manufacturing a Valve Prosthesis Delivery System

Methods for implanting an aortic valve prosthesis using the delivery system described herein involve non-surgical delivery and implantation of an aortic valve prosthesis wherein a self-expandable implant with prosthetic leaflets is flexibly coupled to a valve anchor, and wherein the support frame and the valve anchor are delivered in a compact condition.

Regardless of the route of administration or access, delivery systems disclosed herein can be operated to release the valve anchor prior to expansion of the support frame. Moreover, the valve anchor may be manipulated and repositioned after expansion to ensure proper placement before expanding or releasing the support frame. Optionally, the system can be operated using any of a variety of imaging techniques, including ultrasound, fluoroscopy, or pulsatile feedback, such as electric pulses or ultrasound pulses. Thus, the valve anchor can be positioned using imaging techniques, if desired.

In some embodiments, the clinician can determine or feel, via tactile pressure, that valve anchor has been properly seated or engaged with the native valve structure to confirm proper positioning of the valve anchor relative to the native valve structure. After proper placement of the valve anchor, the support frame can be moved distally along the longitudinal axis toward the valve anchor had eventually be positioned approximately concentric with the valve anchor. At this time, the support frame may be released, and the delivery system can be removed from the patient. The support frame can be implanted over the existing native valve leaflets.

Figure 7A:
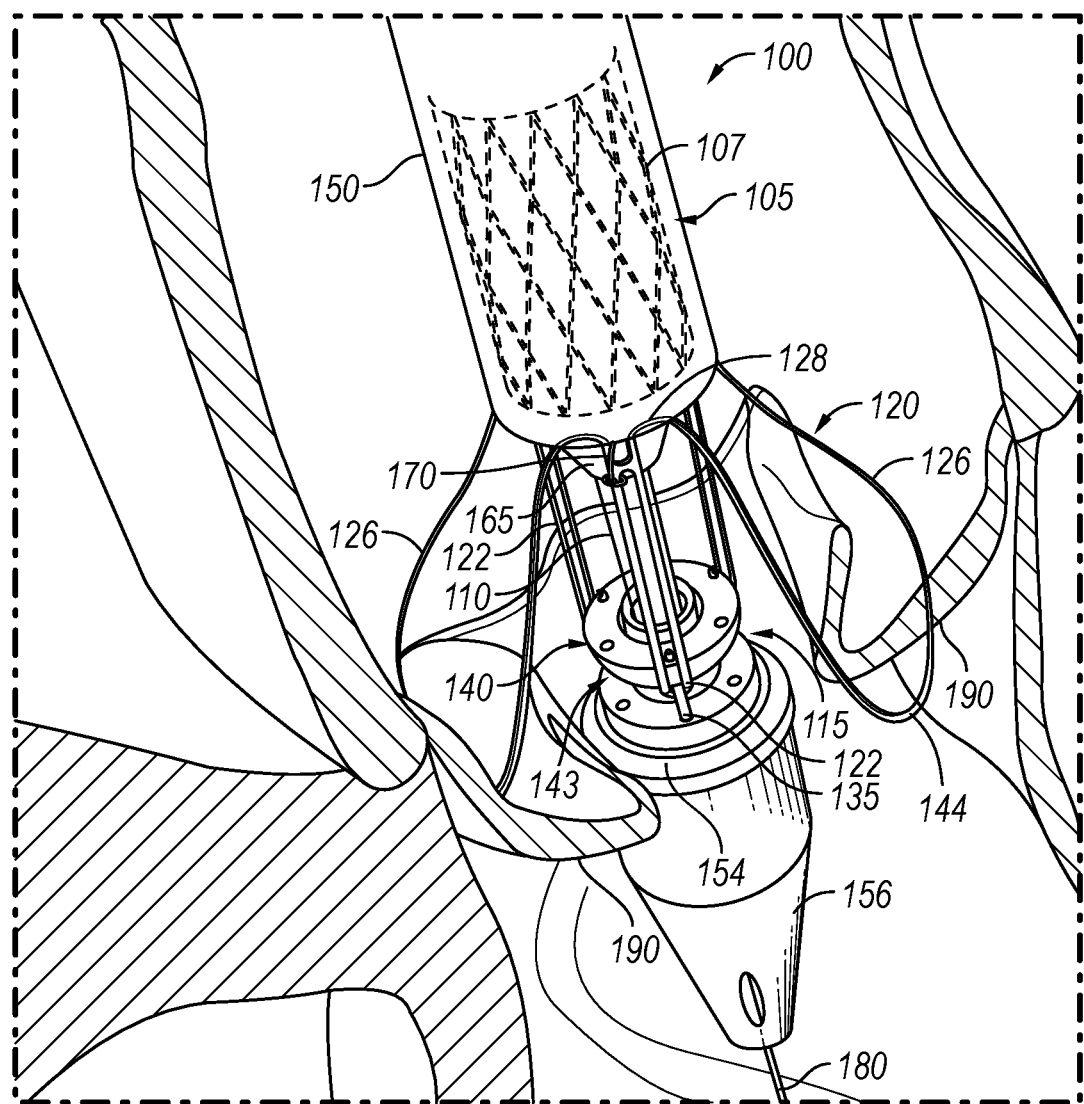
FIGS. 7A-7F illustrate steps in a method for delivering the valve prosthesis through the aorta to the native aortic valve using a valve prosthesis delivery system, according to some embodiments.

FIGS. 7A-7F illustrate a method for operating a valve prosthesis delivery system. The delivery system can be advances through the aorta to the native aortic valve using a delivery system, such as the embodiment described above in FIGS. 6A-6F. As shown in FIG. 7A, in some embodiments, a guiding mechanism, e.g., a guidewire 180 may be advanced towards the target location and fed through the core member 110 to permit the delivery system 100 to advance toward the target location along the guidewire 180. Entry of the delivery system 100 into the vasculature can occur through a variety of paths. However, as described in the present disclosure, the guidewire 180 can be introduced into the aorta and advanced towards the aortic arch. The delivery system 100 can then be advanced along the guide wire 180 until reaching the target location, e.g., the aortic valve of the heart.

FIG. 7A illustrates the delivery system 100 after reaching the aortic valve. As discussed above with regard to FIGS. 6A-6F, the delivery system 100 can be delivered to the target location a delivery configuration (FIG. 6A) and later manipulated to permit expansion of various components of the valve prosthesis 105.

As described above, FIG. 6A illustrates the delivery system 100 as it is configured prior to inserting the delivery system into the patient and during advancement of the delivery system through the patient's vasculature toward the target location. The valve prosthesis 105 is packed within the delivery system 100 in a compact configuration such that the support frame 107 and the valve anchor 120 of the valve prosthesis 105 are packed serially within the sheath 150. As is normal practice, the guidewire is first introduced into the patient, e.g., into the femoral artery or, if using a transapical procedure, into the left ventricle, and advanced to the appropriate heart chamber, past or beyond the native cardiac valve in need of repair. Although not illustrated in the figures, the present disclosure can also provide for transapical delivery of the valve prosthesis 105.

A method of delivering a valve prosthesis to a target location having a damaged or defective valve includes advancing the delivery system 100 into a blood vessel, e.g., the aorta, to position the valve anchor 120 at the target location. In some embodiments, the target location is a position adjacent to an aortic valve of a patient's heart. In particular, the target location may be a position directly above the native aortic leaflets 190, as illustrated in FIG. 7A. The advancing of the delivery system 100 may be achieved by advancing a distal end thereof to the target location in a direction opposite to that of blood flow.

Once the delivery system has been advanced into the blood vessel, the clinician can control the delivery system 100 by actuating one or more actuators on the control unit. In some embodiments, the actuator(s) may be, but is not limited to a knob, a lever, a trigger, a slider, a button, and/or a handle of the control unit. Actuation of the actuator can cause the sheath 150 to retract proximally and reveal at least a portion of the valve anchor 120 at the target location (as shown in FIGS. 6A to 6B and 7A). Proximal retraction of the sheath 150 permits the U-shaped members 126 of the valve anchor 120 to expand at the target location for positioning the valve anchor 120 in a desired orientation. As portions of the U-shaped member 126 are exposed, they will tend to expand radially away from the central axis (or guidewire axis). The radial extension of the U-shaped members 126 can permit the clinician to at least initially align, position, and/or rotate the delivery system 100 into proper alignment within the native valve. In some situations, advancement of the delivery system 100 through the native vasculature can tend to cause the U-shaped member to bend backwards or evert in a direction opposite that shown in FIG. 7A. In such situations, if the sheath 150 is retracted only partially from over the valve anchor 120, the sheath 150 can be distally advanced relative to the valve anchor 120 to push or urge the U-shaped members into a forward-pointing or non-everted orientation, as shown in FIG. 7A.

Figure 7B:
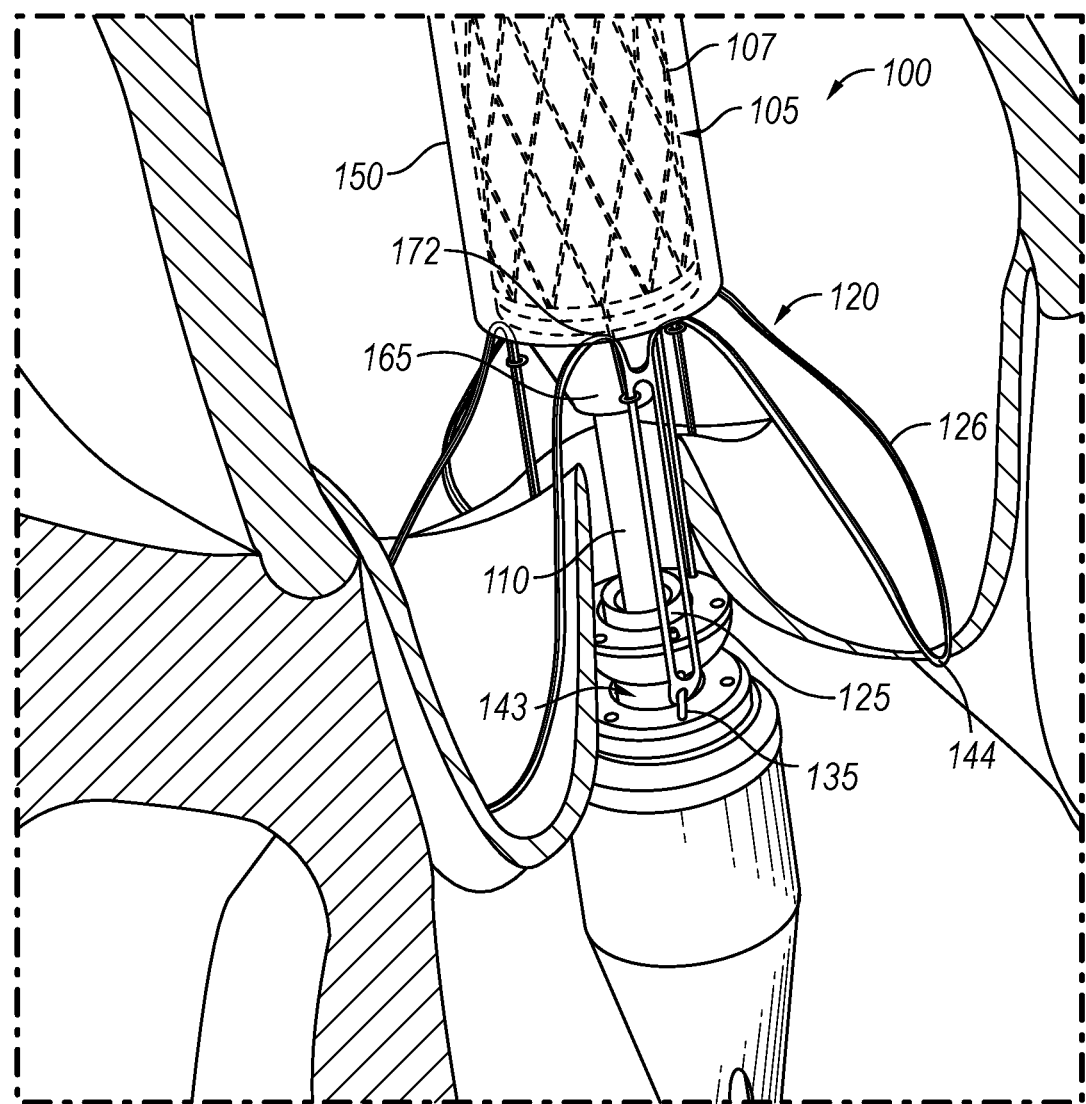

FIG. 7A illustrates placement of the distal end of delivery system 100 including the nose cone 156 within the aorta past the native aortic valve. The distal end section of the delivery system 100, including the nose cone 156, can be advanced and positioned in the aorta past the native aortic valve leaflets 190. As shown in FIGS. 7A and 7B, after properly positioning the valve sheath 150, which houses the valve prosthesis 105, within the aorta, the valve sheath 150 can be pulled in a proximal direction to uncover the valve anchor 120. This allows the base portions 144 of the U-shaped members 126 of the valve anchor 120 to radially expand towards the interior wall of the aorta.

In some embodiments, as discussed herein, the base portions 144 of the valve anchor 120 function as "feelers" which allow the clinician to properly place the valve anchor 120 and support frame 107 within the native valve structure with minimal or no imaging during the time of expansion (see FIGS. 7A and 7B). The valve anchor 120 may be made of, but not limited to, a shape memory material or metal, such as nitinol, as discussed herein.

In some embodiments, the delivery system 100 is further advanced distally and/or rotates until the valve anchor 120 gently sits in the native aortic structure, such as the annulus or sinuses, at the target location. While the valve anchor 120 is advanced distally, it rotates and can self-align according to the anatomical orientation of the native aortic leaflets 190, as shown in FIG. 7B.

After the valve anchor 120 is properly seated or positioned relative to the native valve structure, the clinician can distally advance the pusher component 165 to contact and distally advance the pin assembly 125 relative to the lock component 140. In some embodiments, the distal advancement of the pusher component 165 comprises distally advancing the pusher block 178 to contact and displace the support frame 107 and the pusher component 165 in a distal direction until contacting the pin assembly 135. This causes an increase in the axial spacing between the lock component 140 and the piston member 136 (not shown), as illustrated by distances D1 and D2 in FIGS. 6C and 6D, thereby distally advancing the pins 135 out of the engagement region 143.

Figure 7C:
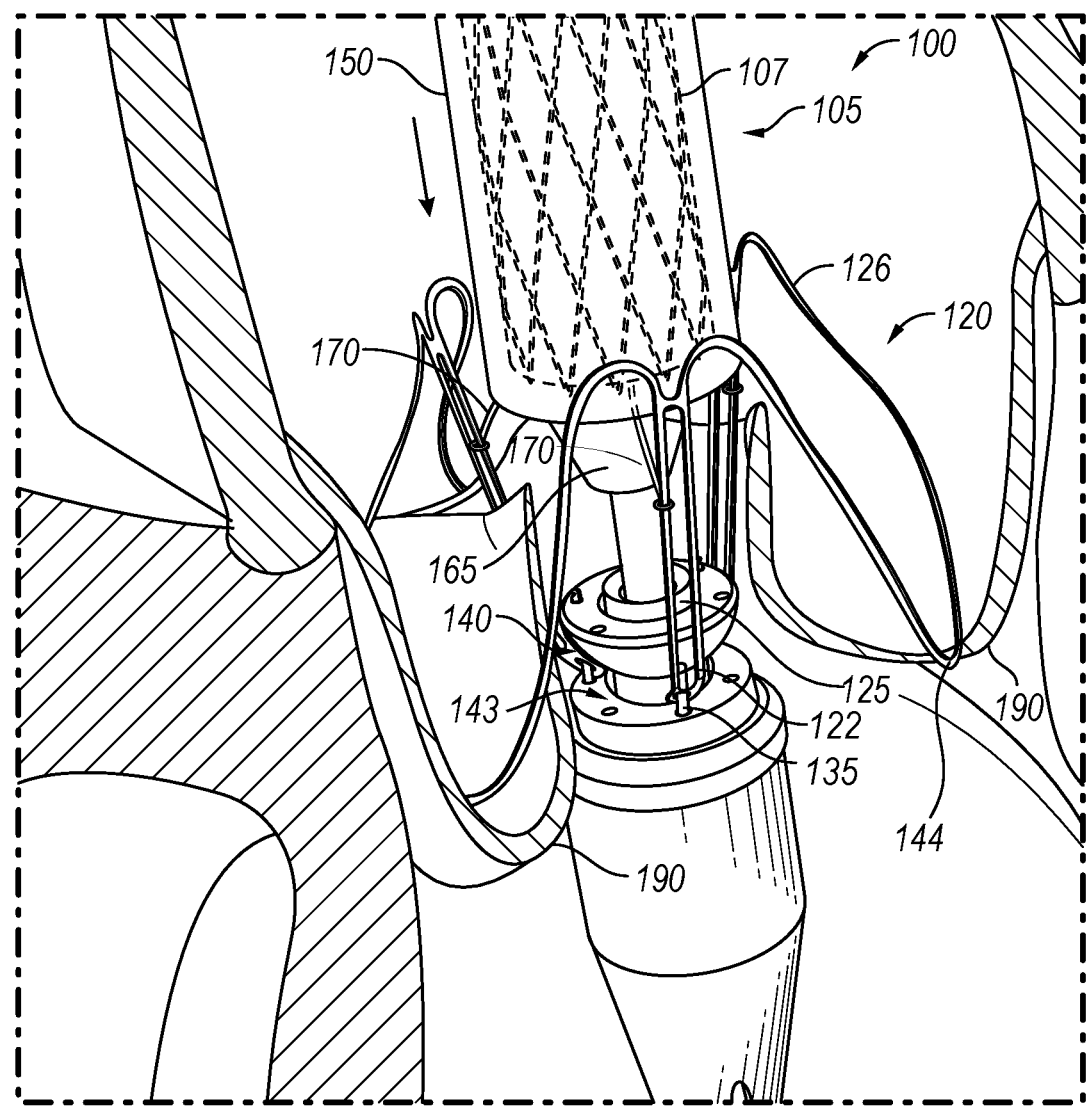
Figure 7D:
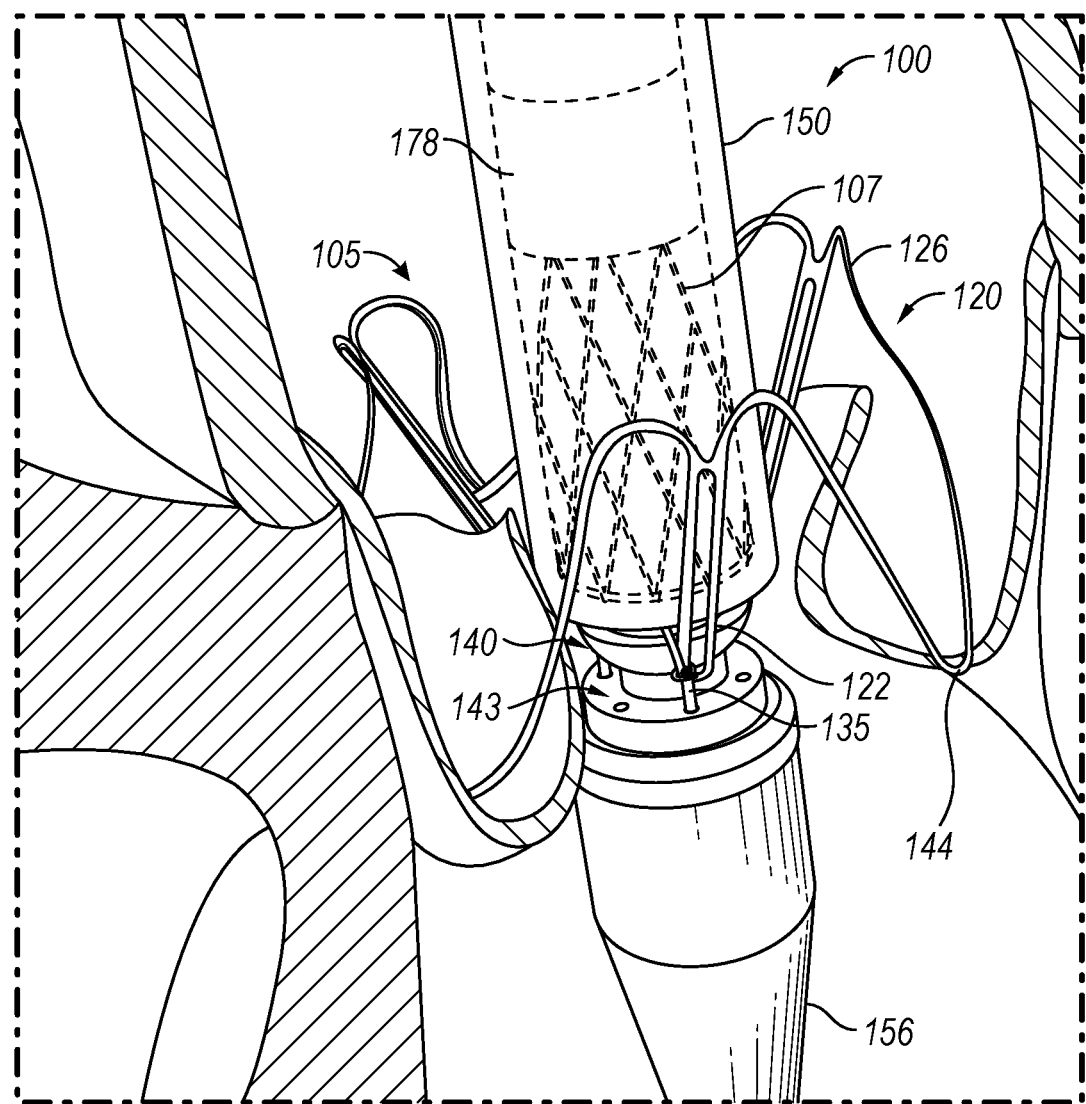

Accordingly, as shown in FIGS. 7C and 7D, in some embodiments, the distally advancement of the pusher component 165 comprises contacting and distally displacing the proximal face 172 of the radial flange 175 (not shown, but see FIGS. 6B-6D) of the pusher component 165 relative to the core member 110, by distally advancing the support frame 107 in the collapsed state by advancing the pusher block 178 and the sheath 150 relative to the core member 110. Distal advancement of the pin assembly 125 relative to the lock component 140 causes the pins 135 of the pin assembly 125 to disengage from the lock aperture 145 of the lock component, thereby permitting release of the valve anchor 120 from the delivery system 100.

Figure 7E:
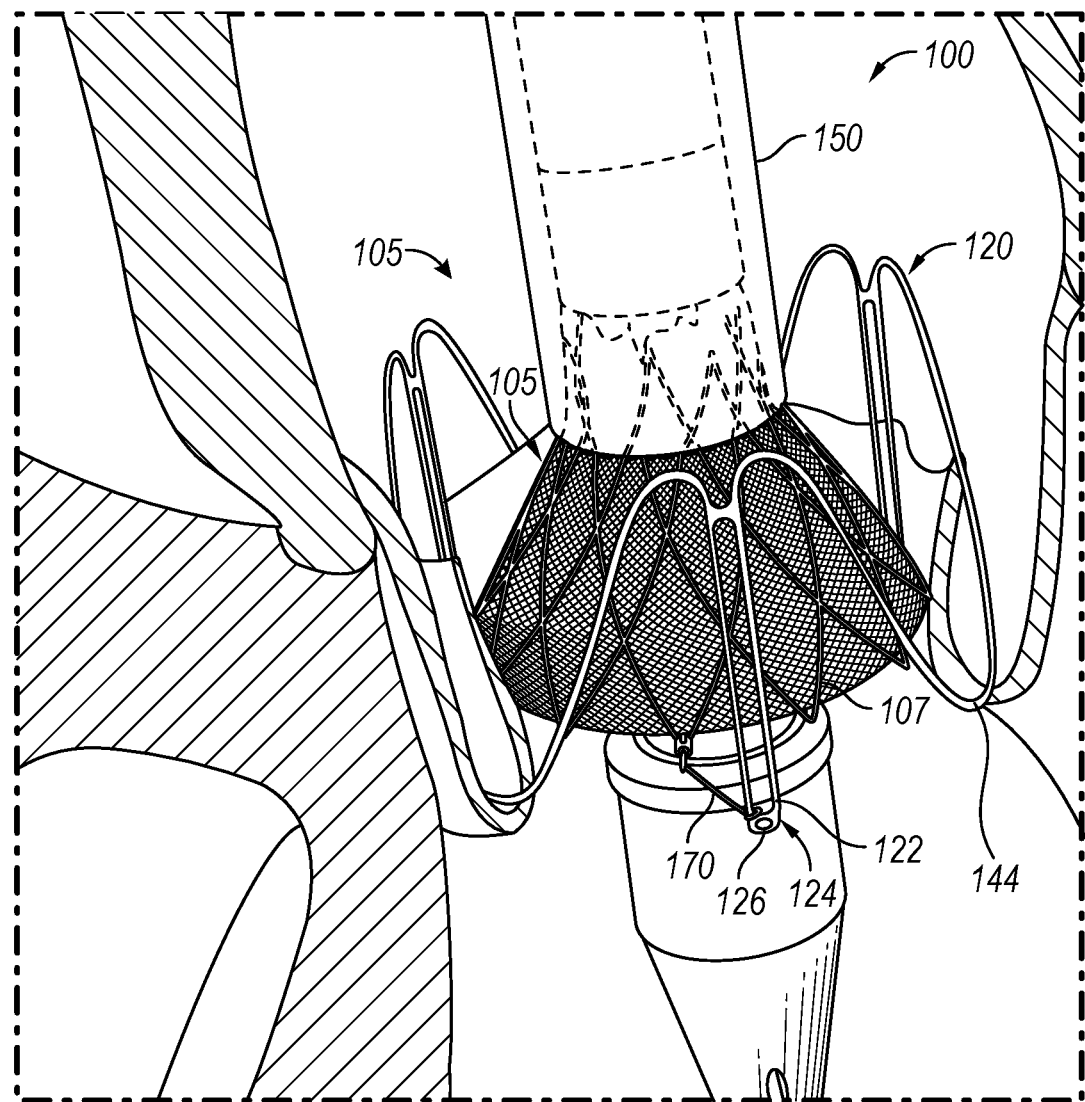
Figure 7F:
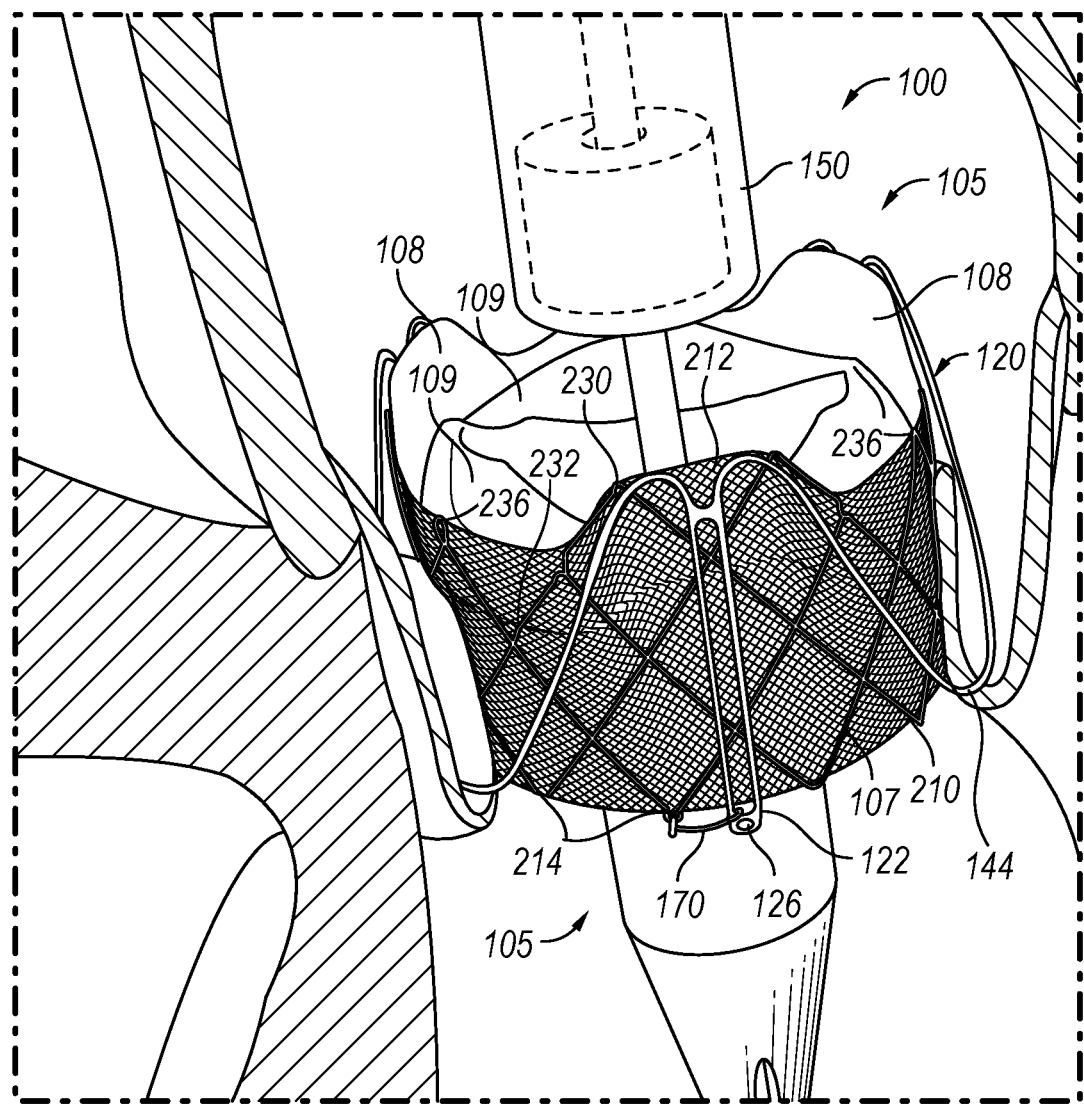

After releasing the anchoring legs 122 of the valve anchor 120 in order to fully release the valve anchor 120, the delivery system 100 can optionally be distally advanced within the valve anchor 120 in order to position the support frame 107 at a desired longitudinal position within the lumen of the valve anchor 120. Thereafter, the valve sheath 150 (which at this time, continues to extend over or cover the support frame 107) can be retracted distally relative to the core member 110 towards the lock component 140, as illustrated in FIGS. 7E and 7F.

In accordance with some embodiments, the delivery system 100 can also be advantageously configured to position portions of the valve anchor 120 on opposing sides of the native valve leaflets. Such an ability enables the delivery system 100 to create a more secure engagement between the valve anchor 120 and the native valve structure. Such configurations and advantages can be achieved by using the engagement mechanism, which can constrain a portion of the anchoring legs of the valve anchor. Further, other embodiments can also provide additional features that facilitate engagement of the opposing sides of the native valve leaflets.

For example, as illustrated in FIG. 7B, the support frame 107 can be slidably coupled to the anchoring leg 122 of the valve anchor 120 via a suture 170, which can create a radial restriction against expansion of the proximal portion of the valve anchor 120. When the support frame 107 is moved distally towards the lock component 140, the suture 170 is accordingly moved distally along the anchoring leg 122 of the valve anchor 120 toward the lock component 140 (see FIGS. 7B-7D). The relief of the radial restriction created by the sutures 170 thereby permits the proximal end portion of the valve anchor 120 to expand radially outwards while holding distal ends of the valve anchor 120 stationary along a longitudinal axis thereof as the valve anchor 120 expands radially. The anchoring legs 122 of the valve anchor 120 can thus be positioned radially inside of or central to the valve leaflets and the base portions 144 of the U-shaped members 126 can be positioned directly against the aortic wall (e.g., within the valve sinuses), radially outside of or about the periphery of the valve leaflets.

Thereafter, the sheath 150 and the support frame 107 are thus advanced distally until distal ends of the sheath 150 and the support frame 107 are positioned directly above the lock component 140. FIG. 7D illustrates a positioning of the support frame 107 in a final, pre-release position. The distal advancement of the sheath 150 and the support frame 107 to the position directly above the lock component 140 also positions the support frame 107 at a pre-release position, which can be adjusted as needed after releasing the valve anchor 120. In some embodiments, the pre-release position is a position in which the support frame 107 is disposed within the sheath 105 and longitudinally within a passage of the valve anchor 120.

When the support frame 107 reaches the final the pre-release position, the clinician can then further advance the pusher component 165 to distally advance the pin assembly 125 and thereby release the valve anchor 120 from engagement with the pin assembly 125. That is, the anchoring legs 122 can be released from being locked or engaged in the engagement region 143 between the lock apertures 145 of the lock component 140 and the connection aperture 127 of the pin assembly 125, as illustrated in FIG. 7E.

FIG. 7E also illustrates the support frame 107 in a partially expanded configuration. After the anchoring legs 122 of the valve anchor 120 are released from being locked between the lock component 140 and the pin assembly 125, the control unit is then activated to retract the sheath 150 proximally along the core member 110 to expose or reveal the support frame 107 and permit the support frame 107 to begin to expand. As the support frame 107 begins to expand, the support frame 107 can be circumferentially constrained (i.e., the rotational orientation of the support frame 107) relative to the valve anchor 120 via the sutures 170. Thus, in some embodiments, the sutures 170 can cause expansion of the support frame 107 can be automatically guided and secured in the proper position by the valve anchor 120.

Referring now to FIG. 7F, the valve prosthesis 105 can comprise a plurality of prosthetic valve leaflets 109 coupled to the support frame 107. The valve leaflets 109 can have surfaces that form a reversibly sealable opening for unidirectional flow of a liquid through the valve prosthesis 105. The valve prosthesis 105 can include three valve leaflets 109 for a tri-leaflet configuration. As appreciated, mono-leaflet, bi-leaflet, and/or multi-leaflet configurations are also possible.

For example, the valve leaflets 109 can be coupled to the support frame 107 to span and control fluid flow through the lumen of the valve prosthesis 105. Further, in some embodiments, the valve prosthesis 105 can comprise a membrane or sealing layer 108 that is coupled to the support frame 107 and the valve leaflets 109. The membrane 108 can tend to ensure that blood flows through the central aperture or lumen of the valve prosthesis 105. The valve prostheses as described herein may be used in various aspects of implantation systems described herein or in any method or system known by one with ordinary skill in the art to implant a valve prosthesis into a subject.

The sealing and anchoring of the valve prosthesis 105 relative to the surrounding native valve structure is also facilitated through the interposition of the native heart valve leaflets 190 between the valve anchor 120 and the support frame 107. This positioning of the valve leaflets 190 facilitates anchoring of the valve prosthesis 105 in the native valve structure and can be applicable to all coronary valves (i.e., aortic, pulmonary, tricuspid and mitral). In some embodiments, the number of valve anchors 120 can be equal to the number of native leaflets 190 within the native valve being treated.

FIG. 7F illustrates the support frame 107 in the fully expanded, released configuration. As illustrated in FIG. 7F, the support frame 107 may be properly placed within the native valve structure when the base portions 144 of the U-shaped members 126 of the valve anchor 120 are approximately adjacent to the distal end of support frame 107. Further, the support frame 107 may be properly placed within the native valve structure when expansion of support frame 107 will result in a sandwiching of the native aortic valve leaflets 190 between the expanded support frame 107 and valve anchor 120.

In some embodiments, after the support frame 107 has been expanded and released within the native valve structure, the control unit may be actuated to retract the rest of the delivery system 100, other than the support frame 107 and the valve anchor 120. For example, the sheath 150 can be distally advanced over the core member 110 to mate the radial depression 154 of the nose cone 156 against the distal end of the sheath 150. In this manner, the delivery system 100 can assume the delivery configuration in which the delivery system 100 has a generally smooth outer profile that will avoid catching or otherwise damaging the vasculature during removal. The delivery system 100 can thereafter be removed from the patient.

Additional Aspects of Valve Prostheses

As also illustrated in FIG. 7F, when expanded and released, the support frame 107 can comprise a first end portion 210 and a second end portion 212. The first end portion 210 can be positioned upstream of the second end portion 212 when the prosthesis 105 is released within the native valve structure.

As illustrated in FIG. 7F, the first end portion 210 of the support frame 107 can be shaped as a generally flat end of a cylinder, where first apices 214 of the support frame 107 lie generally in a common plane, which can be oriented substantially perpendicular relative to a longitudinal axis of the prosthesis 105.

Optionally, the second end portion 212 can be shaped to include a series of peaks 230 and valleys 232, where second apices 236 of the support frame 107 collectively form contours of the peaks 230 and valleys 232. The peaks 230 and valleys 232 of the second end portion 212 can be positioned downstream of the first end portion 210 when the prosthesis is seated within the native valve annulus. In accordance with some embodiments, the prosthetic leaflets 109 can be coupled relative to the support frame 107 at locations circumferentially aligned with the peaks 230 of the second end portion 212, as shown in FIG. 7F. This unique configuration can advantageously enable the prosthesis 100 to more fully approximate the native valve structures, permit a more natural blood flow without limiting or otherwise constraining movement of the valve leaflets 109, and more seamlessly integrate with surrounding architecture of the heart.

In some embodiments, at the second end portion 212, an axial end of the membrane 108 can be shaped to cover the major peaks 230 and valleys 232 of the second end portion 212. In some embodiments, the membrane 108 can be shaped to cover the second apices or minor peaks 236 within the valleys 232 between the major peaks 230. Advantageously, the configuration of the minor peaks 236 between the major peaks 230 can allow improved access to and prevent obstructions of the ostia compared to prior art valve prostheses.

A prior art valve prosthesis, implanted within an aorta may block or obstruct the coronary ostia disposed a distance away from the valve annulus due to the geometry of the valve frame and the membrane, as discussed in Applicant's U.S. Patent Application No. 62/614,488, filed on Jan. 7, 2018 (122271-5025), U.S. Patent Application No. 62/614,489, filed on Jan. 7, 2018 (122271-5040), U.S. Patent Application No. 62/756,556, filed on Nov. 6, 2018 (122271-5127), and U.S. Patent Application No. 62/781,537, filed on Dec. 18, 2018 (122271-5129), the entireties of which are incorporated herein by reference.

Referring to FIG. 7F, the difference in height between the major peaks 230 and the minor peaks 236 facilitates access to the coronary ostia while allowing for desired operation of the valve prosthesis 105. In some embodiments, the minor peaks 236 are configured to be low enough to allow a variety of sizes and locations of the coronary ostia with respect to the native valve annulus location of a patient. Advantageously, in some embodiments, the minor peaks 236 allow for access to ostia that are less than 10 mm, less than 8 mm, or less than 6 mm in coronary ostia height, which are typically excluded by conventional available prostheses. The ostia height can be measured as the vertical distance between the inferior edge of the coronary artery ostium and the aortic annular plane. Further, in some embodiments, the minor peaks 236 allow for access to ostia that are disposed at a lower axial distance (or ostia height) relative to the valve annulus. Furthermore, in some embodiments, the valve prosthesis 105 can be arranged to be disposed lower in the valve annulus to allow greater access to the ostia. By providing minor peaks 236 between the major peaks 230, and optionally used with one or more other features discussed herein, access to the coronary ostia is preserved allowing for future procedures that may require access to the ostia, such as coronary stenting.

In accordance with some embodiments, the axial length of the support frame 107 can vary between the major peaks 230, the minor peaks 236, and the valleys 232.

For example, the axial length of the support frame 107 measured at the major peaks 230 can be about 10% to about 50%, about 20% to about 40%, about 25% to about 35%, or about 33% greater than the axial length measured at the minor peaks 236.

Additionally, in some embodiments, the axial length of the support frame 107 measured at the major peaks 230 can be about 50% to about 150%, about 70% to about 130%, about 90% to about 110%, or about 100% greater than the axial length measured at the valleys 232.

Further, in some embodiments, although the membrane 108 is illustrated as following the major peaks 230 and the minor peaks 236 along the second end portion 212 of the support frame 107, the membrane 108 can also extend along the individual struts or frame members of the support frame 107. Thus, the individual struts forming the support frame 107 can define approximately the boundary of the membrane 108.

Additional aspects of the support frame 107, the membrane 108, and valve anchor 120 can be configured as discussed and illustrated in some of Applicant's copending applications noted above, the entirety of which is incorporated herein by reference.

For example, in some embodiments, the membrane 108 can be formed or manufactured by cutting the membrane 108 from a woven or mesh fabric. The membrane fabric can be a fabric formed from woven fiber, such as woven polyester. As discussed and illustrated in some of Applicant's copending applications noted above, the membrane fabric can be woven together with fibers in a warp direction and a weft direction that are oriented transverse, and in some cases, perpendicular, relative to each other. In some embodiments, a fabric may resist stretching in the warp and weft directions while allowing stretching and compliance in directions oblique to or biased from the warp and weft directions. The membrane 108 and frame 107 can be configured as also disclosed in some of Applicant's copending applications noted above.

Optionally, one or more membranes 108 can be cut from the membrane fabric using templates that are generally in the shape of the membrane. One or more templates can be placed on the membrane fabric to cut out the membrane. The template can be oriented at an angle relative to the membrane fabric so that the membrane, when coupled to the support frame 107, defines a bias angle between the warp or weft directions of the fibers of the membrane and the longitudinal axis of the support frame 107. The bias angle can be from about 30 degrees to about 60 degrees, such as about 35 degrees, about 40 degrees, about 45 degrees, about 50 degrees, or about 55 degrees.

In some embodiments, the warp and weft of the woven membrane 108 can be oriented relative to the longitudinal axis at a bias angle between 0 and 90 degrees. In some embodiments, the woven membrane 108 can be oriented at a bias angle between about 15 and about 75 degrees relative to the longitudinal axis. In some embodiments, the woven membrane 108 can be oriented at a bias angle between about 30 degrees and about 60 degrees relative to the longitudinal axis. In some embodiments, the woven membrane 108 can be oriented at a bias angle of about 45 degrees relative to the longitudinal axis.

By orienting the templates at a bias angle relative to the membrane fabric, the resulting membrane 108 can be cut on the bias with the bias angle with respect to the warp and weft directions of the membrane fabric. In some embodiments, the membrane 108 can be cut at the bias angle by spiral wrapping the membrane fabric onto the support frame 107 and cutting the membrane fabric.

Through implementation of a bias orientation of fibers of the membrane 108 on the support frame 107, the membrane 108 can more easily radially compress and axially elongate in tandem with the support frame 107, thus permitting the membrane 108 and the support frame 107 to operate as a single unit, in some embodiments. Similarly, in some embodiments, by orienting the membrane 108 along a bias angle, the membrane 108 can more readily elongate along longitudinal axis to obtain a smaller cross-sectional profile, which can prevent flaring, bunching, or pleating, thereby minimizing the cross-sectional profile of the valve prosthesis 105 in a compressed configuration.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method of assembly for valve prosthesis delivery, the method comprising: housing a valve prosthesis in a compacted state within a sheath of a delivery system, the valve prosthesis comprising a valve anchor and a support frame coupled to the valve anchor, the valve anchor comprising a plurality of anchoring legs having a plurality of connection apertures; slidably coupling a pin assembly around a core member so that the pin assembly is slidable longitudinally along the core member; and inserting a plurality of pins of the pin assembly through the plurality of connection apertures of the valve anchor and a plurality of lock apertures of the delivery system to engage the plurality of anchoring legs of the valve anchor.

Clause 2. The method of Clause 1, further comprising: positioning the plurality of connection apertures of the valve anchor between a first flange and a second flange, wherein the lock apertures extend through both the first flange and the second flange.

Clause 3. The method of Clause 1, further comprising: positioning an annular component of the pin assembly within a cavity of the delivery system so that the pin assembly is reciprocal within the cavity between an engaged configuration and a disengaged configuration, wherein the plurality of pins extend longitudinally from the annular component.

Clause 4. The method of Clause 1, further comprising: slidably coupling a pusher component around the core member so that the pusher component is slidable longitudinally along the core member.

Clause 5. The method of Clause 4, further comprising: positioning a tubular component of the pin assembly to extend along the core member towards the pusher component so that the pusher component can contact an end of the tubular component.

Clause 6. The method of Clause 4, further comprising: positioning a tubular component of the pusher component to extend along the core member towards the pin assembly so that the tubular component can contact the pin assembly.

Clause 7. The method of Clause 4, further comprising: positioning the pusher component at a first end of the support frame so that the first end of the support frame can contact the pusher component.

Clause 8. The method of Clause 7, further comprising: positioning a pushing block at a second end of the support frame opposite to the first end of the support frame so that the second end can contact the support frame.

Clause 9. The method of Clause 1, further comprising: coupling the valve anchor to the support frame via at least one suture slidably coupled along a plurality of longitudinal slots extending along a length of the plurality of anchoring legs.

Clause 10. The method of Clause 1, further comprising: positioning the valve anchor and the support frame coupled to the valve anchor serially within the sheath.

Clause 11. A delivery system comprising: a sheath having a valve prosthesis housed therein in a compacted state, wherein the valve prosthesis comprises a valve anchor and a support frame movably coupled to the valve anchor, wherein the valve anchor comprises a plurality of anchoring legs having a plurality of connection apertures; a core member extending longitudinally; a lock component comprising a plurality of lock apertures; and a pin assembly slidably coupled to the core member so that the pin assembly is slidable longitudinally along the core member, wherein the pin assembly comprises a plurality of pins extending longitudinally through the plurality of connection apertures and through the plurality of lock apertures to engage the plurality of anchoring legs of the valve anchor.

Clause 12. The delivery system of Clause 11, further comprising: positioning the plurality of connection apertures of the valve anchor between a first flange and a second flange, wherein the lock apertures extend through both the first flange and the second flange.

Clause 13. The delivery system of Clause 11, wherein the pin assembly further comprises an annular component reciprocably disposed within a cavity, wherein the plurality of pins extend longitudinally from the annular component.

Clause 14. The delivery system of Clause 11, further comprising: a pusher component slidably coupled to the core member so that the pusher component is slidable longitudinally along the core member.

Clause 15. The delivery system of Clause 14, wherein the pin assembly comprises a tubular component extending along the core member towards the pusher component, wherein the pusher component is configured to contact an end of the tubular component.

Clause 16. The delivery system of Clause 14, wherein the pusher component comprises a tubular component extending along the core member towards the pin assembly, wherein an end of the tubular component is configured to contact the pin assembly.

Clause 17. The delivery system of Clause 14, wherein the support frame has a first end positioned to contact the pusher component.

Clause 18. The delivery system of Clause 17, further comprising: a pushing block configured to contact a second end of the support frame opposite to the first end of the support frame.

Clause 19. The delivery system of Clause 11, further comprising: at least one suture coupled to the support frame and slidably coupled to along a plurality of longitudinal slots extending along a length of the plurality of anchoring legs.

Clause 20. The delivery system of Clause 11, wherein the valve anchor and the support frame coupled to the valve anchor are positioned serially within the sheath.

Clause 21. A delivery system comprising: a sheath having a valve prosthesis housed therein in a compacted state, wherein the valve prosthesis comprises a valve anchor and a support frame movably coupled to the valve anchor, wherein the valve anchor comprises a plurality of rounded base portions and a plurality of anchoring legs interconnected with and alternatingly interposed between the plurality of rounded base portions, wherein each of the anchoring legs has a proximal end joined to a rounded base portion and a distal end having a connection aperture; a core member extending longitudinally; a lock component comprising a plurality of lock apertures; and a pin assembly positioned distal to the support frame and slidably coupled to the core member, wherein the pin assembly comprises a plurality of pins extending proximally through the plurality of connection apertures and through the plurality of lock apertures to engage the plurality of anchoring legs of the valve anchor.

Clause 22. The delivery system of Clause 21, further comprising: positioning the connection apertures of the valve anchor between a distal flange and a proximal flange, wherein the lock apertures extend through both the distal flange and the proximal flange.

Clause 23. The delivery system of Clause 21, wherein the pin assembly further comprises an annular component reciprocably disposed within a cavity, wherein the pin assembly is reciprocal between an engaged configuration at a proximal position within the cavity and a disengaged configuration at a distal position within the cavity, wherein the plurality of pins extend proximally from a proximal face of the annular component.

Clause 24. The delivery system of Clause 21, further comprising: a pusher component slidably coupled to the core member so that the pusher component is slidable longitudinally along the core member.

Clause 25. The delivery system of Clause 24, wherein the pin assembly comprises a tubular component extending proximally along the core member towards the pusher component, wherein the pusher component is configured to contact a distal face of the tubular component.

Clause 26. The delivery system of Clause 24, wherein the pusher component comprises a tubular component extending distally along the core member towards the pin assembly, wherein an end of the tubular component is configured to contact a proximal face of the pin assembly.

Clause 27. The delivery system of Clause 24, wherein the support frame has a distal end positioned to contact a proximal face of the pusher component.

Clause 28. The delivery system of Clause 27, further comprising: a pushing block configured to contact a proximal end of the support frame opposite to the distal end of the support frame.

Clause 29. The delivery system of Clause 21, further comprising: at least one suture coupled to the support frame and slidably coupled to along a plurality of longitudinal slots extending along a length of the plurality of anchoring legs.

Clause 30. The delivery system of Clause 21, wherein the valve anchor and the support frame coupled to the valve anchor are positioned serially within the outer sheath so that the valve anchor is disposed distal to the support frame.

Clause 31. A method for delivering a valve prosthesis to a target location in a vessel of a subject, the method comprising: introducing a delivery system into the vessel to position a valve anchor at the target location; proximally retracting a sheath of the delivery system to permit anchoring members of the valve anchor to expand for anchoring the valve anchor at the target location while maintaining engagement between an anchoring leg of the valve anchor and an engagement mechanism of the delivery system, the engagement mechanism comprising a pusher component, a pin assembly, and a lock component; and distally advancing the pusher component relative to a core member of the delivery system to contact and distally advance the pin assembly relative to the lock component to disengage the pin assembly from the lock component, thereby permitting release the anchoring leg of the valve anchor from the delivery system.

Clause 32. The method of Clause 31, wherein the anchoring member comprises a U-shaped member, and wherein the method further comprises advancing the anchoring members into respective valve structures at the target location.

Clause 33. The method of Clause 32, wherein the target location comprises an aortic valve and the valve structures comprise aortic valve sinuses.

Clause 34. The method of Clause 31, wherein the method further comprises distally advancing the anchoring members into the target location.

Clause 35. The method of Clause 31, wherein the method further comprises rotating the anchoring members at the target location.

Clause 36. The method of Clause 31, wherein the method further comprises proximally withdrawing the anchoring members at the target location.

Clause 37. The method of Clause 31, wherein the pin assembly comprises a pin that extends through an engagement region and a lock aperture of the lock component in an engaged configuration to engage the anchoring leg within the engagement region, and wherein the distally advancing comprises advancing the pin of the pin assembly through the lock aperture and through the engagement region to permit disengagement of the anchoring leg.

Clause 38. The method of Clause 31, wherein the pin assembly comprises a tubular component extending proximally from the pin assembly along the core member, and wherein the distally advancing comprises contacting a distal surface of the pusher component against a proximal surface of the tubular component.

Clause 39. The method of Clause 31, wherein the pin assembly comprises a piston member and the lock component comprises a cavity, wherein the distally advancing comprises causing the piston member to move distally within the cavity.

Clause 40. The method of Clause 31, wherein the introducing comprises positioning the valve anchor adjacent to an aortic valve of a patient's heart.

Clause 41. The method of Clause 40, wherein the proximally retracting permits the anchoring members to expand into an annulus of the aortic valve.

Clause 42. The method of Clause 31, further comprising, after the valve anchor is released, expanding a support frame of the valve prosthesis within a lumen of the valve anchor.

Clause 43. The method of Clause 42, wherein the expanding comprises proximally retracting the sheath from over the support frame to permit the support frame to self-expand within the valve anchor.

Clause 44. The method of Clause 31, wherein a distal end portion of the delivery system is advanced to a defective valve at the target location in a direction opposite to that of blood flow.

Clause 45. The method of Clause 31, wherein the proximally retracting the sheath is performed while holding a support frame of the valve prosthesis stationary along a longitudinal axis of the valve prosthesis until the support frame expands radially.

Further Considerations

In some embodiments, any of the clauses herein may depend from any one of the independent clauses or any one of the dependent clauses. In some embodiments, any of the clauses (e.g., dependent or independent clauses) may be combined with any other one or more clauses (e.g., dependent or independent clauses). In some embodiments, a claim may include some or all of the words (e.g., steps, operations, means or components) recited in a clause, a sentence, a phrase or a paragraph. In some embodiments, a claim may include some or all of the words recited in one or more clauses, sentences, phrases or paragraphs. In some embodiments, some of the words in each of the clauses, sentences, phrases or paragraphs may be removed. In some embodiments, additional words or elements may be added to a clause, a sentence, a phrase or a paragraph. In some embodiments, the subject technology may be implemented without utilizing some of the components, elements, functions or operations described herein. In some embodiments, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the term "distal" can denote a location or direction that is away from a point of interest, such as a control unit or region of the delivery system that will be used to deliver a valve prosthesis to a native valve annulus. Additionally, the term "proximal" can denote a location or direction that is closer to a point of interest, such as a control unit or region of the delivery system that will be used to deliver a valve prosthesis.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A delivery system comprising:
    a sheath having a valve prosthesis housed therein in a compacted state, wherein the valve prosthesis comprises a valve anchor and a support frame movably coupled to the valve anchor, wherein the valve anchor comprises a plurality of rounded base portions and a plurality of anchoring legs interconnected with and alternatingly interposed between the plurality of rounded base portions, wherein each of the anchoring legs has a proximal end joined to one of the plurality of rounded base portions and a distal end having a connection aperture;
    a core member extending longitudinally;
    a lock component comprising a plurality of lock apertures;
    a pin assembly positioned distal to the support frame and slidably coupled to the core member, wherein the pin assembly comprises a plurality of pins extending proximally through the plurality of connection apertures and through the plurality of lock apertures to engage the plurality of anchoring legs of the valve anchor and an annular component reciprocably disposed within a cavity, wherein the annular component is reciprocal between an engaged configuration at a proximal position within the cavity and a disengaged configuration at a distal position within the cavity, wherein the plurality of pins extend proximally from a proximal face of the annular component; and
    a pusher component slidable along the core member and relative to the lock component.

2. The delivery system of claim 1, wherein the pusher component is slidable longitudinally along the core member.

3. The delivery system of claim 2, wherein the pin assembly comprises a tubular component extending proximally along the core member towards the pusher component, wherein the pusher component is configured to contact a distal face of the tubular component.

4. The delivery system of claim 2, wherein the pusher component comprises a tubular component extending distally along the core member towards the pin assembly, wherein an end of the tubular component is configured to contact a proximal face of the pin assembly.

5. A delivery system comprising:
    a core member for carrying a valve prosthesis therealong;
    a lock component fixedly coupled to the core member and comprising a plurality of lock apertures;
    a pusher component slidably relative to the core member and the lock component to contact a pin assembly; and
    the pin assembly positioned distal to the pusher component and slidably coupled to the core member, wherein the pin assembly comprises a plurality of pins extending proximally through the plurality of lock apertures for engaging the valve prosthesis therewith, the pin assembly being moveable along the core member in response to contact from the pusher component for causing the plurality of pins to exit the lock apertures and disengage with the valve prosthesis, wherein the lock component is coupled to a nose cone that is fixedly coupled to the core member and the nose cone comprises a cavity and pin assembly is disposed and movable within the cavity.

6. The delivery system of claim 5, further comprising a sheath extending proximal to the pusher component.

7. A delivery system comprising:
    a sheath having a valve prosthesis housed therein in a compacted state, the valve prosthesis comprising a valve anchor and a support frame movably coupled to the valve anchor, the valve anchor comprising a plurality of anchoring legs each having a connection aperture;
    a core member extending longitudinally;
    a lock component comprising a plurality of lock apertures;
    a pin assembly positioned distal to the support frame and slidably coupled to the core member, wherein the pin assembly comprises a plurality of pins extending proximally through the plurality of connection apertures and through the plurality of lock apertures to engage the plurality of anchoring legs of the valve anchor; and
    a pusher component slidable longitudinally along the core member and relative to the lock component and the pusher component comprises a tubular component extending distally along the core member towards the pin assembly, wherein an end of the tubular component is configured to contact a proximal face of the pin assembly.

* * * * *